United States Patent [19]

Altmann et al.

[11] Patent Number: 5,461,152
[45] Date of Patent: Oct. 24, 1995

[54] CARBOCYCLIC NUCLEOSIDES CONTAINING BICYCLE RINGS, OLIGONUCLEOTIDES THEREFROM, PROCESS FOR THEIR PREPARATION, THEIR USE AND INTERMEDIATES

[75] Inventors: Karl-Heinz Altmann, Basel; René Imwinkelried, Brig-Glis; Albert Eschenmoser, Küsnacht, all of Switzerland

[73] Assignee: Ciba-Geigy Corporation, Ardsley, N.Y.

[21] Appl. No.: 83,812

[22] Filed: Jun. 28, 1993

[30] Foreign Application Priority Data

Jul. 1, 1992 [CH] Switzerland ............................ 2075/92

[51] Int. Cl.$^6$ .................. C07F 9/02; C07D 473/00; C07D 239/02; A61K 31/695
[52] U.S. Cl. .................. 544/229; 544/243; 544/244; 544/276; 544/277; 544/264; 544/311; 544/312; 544/313; 544/314; 544/317; 544/318; 544/323; 544/325; 544/329; 514/63; 514/81; 514/86; 514/258; 514/269; 514/274; 514/303; 546/118; 564/460
[58] Field of Search ..................... 514/269, 274; 544/229, 243, 311–314, 317, 318, 323, 325, 329

[56] References Cited

FOREIGN PATENT DOCUMENTS

| 267878 | 5/1988 | European Pat. Off. |
| 266099 | 5/1988 | European Pat. Off. |
| 278501 | 8/1988 | European Pat. Off. |
| 8707300 | 12/1987 | WIPO |
| 8908146 | 9/1989 | WIPO |
| 9106556 | 5/1991 | WIPO |

OTHER PUBLICATIONS

J. Balzarini et al. J. Med. Chem. 32:1861–1865 (1989).
A. D. Borthwick et al. Tetrahedron vol. 48 No. 4, pp. 571–623 (1992).
M. R. Harnden et al. J. Med. Chem. 33, pp. 187–196 (1990).
C. Héléne et al. Biochimica et Biophysica Acta, 1049 pp. 99–125, (1990).
M. Koga et al. Tetrahedron letters vol. 31, No. 41, pp. 5861–5864 (1990).
G. Madhavan et al. J. Org. Chem. vol. 51 pp. 1287–1293 (1986).
V. E. Marquez et al. Medicinal Res. Review vol. 6, No. 1, pp. 1–40 (1986).
M. D. Matteucci et al. vol. 26 pp. 287–296 (1991).
Y. F. Shealy et al. J. Heterocyclic Chem. vol. 18, 383 (1981).
E. Uhlmann et al. Chemical Reviews vol. 90, No. 4, pp. 543–584 (1990).

*Primary Examiner*—Cecilia Tsang
*Attorney, Agent, or Firm*—Kevin T. Mansfield; George R. Dohmann

[57] ABSTRACT

Compounds of the formulae I and Ia and their racemates

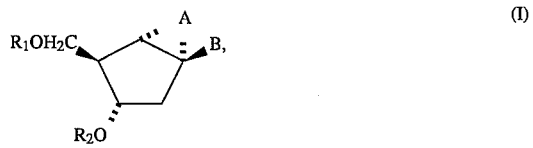

(I)

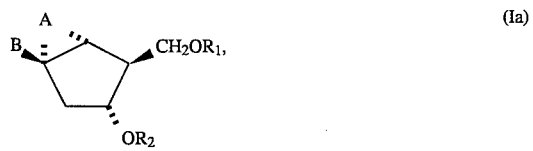

(Ia)

in which A is —$CH_2$— or —$CH_2CH_2$—, $R_1$ is hydrogen or a protective group, $R_2$ is hydrogen or a protective group or a radical forming a phosphorus-containing nucleotide bridge group and B is a purine or pyrimidine radical or an analogue thereof, can be used as antiviral active ingredients or for the preparation of biologically active oligonucleotides.

13 Claims, No Drawings

CARBOCYCLIC NUCLEOSIDES CONTAINING BICYCLE RINGS, OLIGONUCLEOTIDES THEREFROM, PROCESS FOR THEIR PREPARATION, THEIR USE AND INTERMEDIATES

The invention relates to nucleoside analogues having a bicyclo[3.1.0]hexane or bicyclo[3.2.0]heptane skeleton, a process for their preparation by synthesis reactions known per se of nuclein bases from the thymine, adenine, purine or cytosine series, 1-amino-3-hydroxy-4-hydroxymethylbicyclo[3.1.0]hexane and 1-amino-3-hydroxy-4-hydroxymethylbicyclo[3.2.0]heptane and their protected derivatives as intermediates, oligonucleotides containing these nucleosides and the use of the nucleosides for the preparation of oligonucleotides containing identical or different nucleoside units in the molecule.

Nucleosides and oligonucleotides have acquired wide interest as antiviral active ingredients or because of their capability to interact with nucleic acids ("antisense" oligonucleotides) and the biological activity associated therewith, see, for example, E. Uhlmann et al., Chemical Reviews 90:543–584 (1990). To provide nucleosides having novel properties or to improve the interaction of antisense oligonucleotides with natural nucleic acids and their stability to nucleases, the sugar radicals of nucleosides (or the nucleotide units in oligonucleotides) or the internucleotide phosphate bond in oligonucleotides have been modified in very different ways, see, for example, V. E. Marquez et al., Medicinal Research Reviews 6:1–40 (1986), C. Hél`ene et al., Biochimica et Biophysica Acta 1049:99–125 (1990), U. Englisch et al., Angewandte Chemie No. 6, 629–646 (1991), M. D. Matteucci et al. in Annual Reports in Medicinal Chemistry, Academic Press Inc., 287–296 (1991) and WO 91/06556. Bicyclic and carbocyclic nucleosides containing 3'-hydroxy and 4'-hydroxymethyl groups have not yet been disclosed for this purpose.

The invention relates to enantiomeric compounds of the formulae I and Ia and their racemates

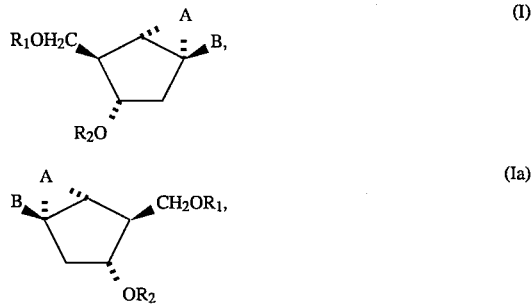

in which A is —$CH_2$— or —$CH_2CH_2$—, $R_1$ is hydrogen or a protective group, $R_2$ is hydrogen or a protective group or a radical forming a phosphorus-containing nucleotide bridge group and B is a purine or pyrimidine radical or an analogue thereof.

Preferred compounds are those in which $R_1$ and $R_2$ are each hydrogen.

In a particularly preferred embodiment, A is —$CH_2$—.

In another preferred embodiment, the compounds are the enantiomers of the formula I.

Protective groups and processes for derivatisation of the hydroxyl groups with such protective groups are generally known in sugar and nucleotide chemistry and described, for example, by B. T. Greene, Protective Groups in Organic Synthesis, Wiley Interscience, New York (1991). Examples of such protective groups are: linear or branched $C_1$–$C_8$alkyl, particularly $C_1$–$C_4$alkyl, for example methyl, ethyl, n- and i-propyl, n-, i- and t-butyl; $C_7$–$C_{18}$aralkyl, for example benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, methoxyphenyl(diphenyl)methyl, di(methoxyphenyl)phenylmethyl, tri(methoxyphenyl)methyl, tri(dimethoxyphenyl)methyl; triphenylsilyl, alkyldiphenylsilyl, dialkylphenylsilyl and trialkylsilyl having 1 to 20, preferably 1 to 12 and particularly preferably 1 to 8, C atoms in the alkyl groups, for example trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl; —($C_1$–$C_8$alkyl)$_2$Si—O—Si($C_1$–$C_8$alkyl)$_2$—, in which alkyl, for example, is methyl, ethyl, n- or i-propyl, n-, i- or t-butyl; $C_2$–$C_{12}$acyl, particularly $C_2$–$C_8$acyl, for example acetyl, propanoyl, butanoyl, pentanoyl, hexanoyl, benzoyl, methylbenzoyl, methoxybenzoyl, chlorobenzoyl and bromobenzoyl; $R_3$—$SO_2$—, in which $R_3$ is $C_1$–$C_{12}$alkyl, particularly $C_1$–$C_6$alkyl, $C_5$— or $C_6$cycloalkyl, phenyl, benzyl, $C_1$–$C_{12}$alkylphenyl and particularly $C_1$–$C_4$alkylphenyl, or $C_1$–$C_{12}$alkylbenzyl and particularly $C_1$–$C_4$alkylbenzyl, or halophenyl or halobenzyl, for example methyl-, ethyl-, propyl-, butyl-, phenyl-, benzyl-, p-bromo-, p-methoxy- or p-methylphenylsulfonyl; unsubstituted or F-, Cl-, Br-, $C_1$–$C_4$alkoxy-, tri($C_1$–$C_4$alkyl)silyl- or $C_1$–$C_4$alkylsulfonyl-substituted $C_1$–$C_{12}$alkoxycarbonyl, preferably $C_1$–$C_8$alkoxycarbonyl, for example methoxy-, ethoxy-, n- or i-propoxy- or n-, i- or t-butoxycarbonyl, 2-trimethylsilylethoxycarbonyl, 2-methylsulfonylethoxycarbonyl, or phenoxycarbonyl or benzyloxycarbonyl which is unsubstituted or substituted as for alkoxycarbonyl, for example methyl- or methoxy- or chlorophenoxycarbonyl or -benzyloxycarbonyl, and also 9-fluorenylmethyloxycarbonyl. If $R_1$ and/or $R_2$ is alkyl, it can be substituted by F, Cl, Br, $C_1$–$C_4$alkoxy, phenoxy, chlorophenoxy, methoxyphenoxy, benzyloxy, methoxybenzyloxy or chlorophenoxy. $R_1$ and $R_2$ in formula I can be identical or different protective groups, identical protective groups often being preferred.

In a preferred embodiment, the compounds of the formula I are those in which $R_1$ and $R_2$ as protective groups are, independently of one another, linear or branched $C_1$–$C_4$alkyl, $C_7$–$C_{18}$aralkyl, trialkylsilyl having 1 to 12 C atoms in the alkyl groups, —($C_1$–$C_4$alkyl)$_2$Si—O—Si($C_1$–$C_4$alkyl)$_2$, $C_2$–$C_8$acyl, $R_3$–$SO_2$—, in which $R_3$ is $C_1$–$C_6$alkyl, phenyl, benzyl, $C_1$–$C_4$alkylphenyl, $C_1$–$C_4$alkylbenzyl, halophenyl or halobenzyl, or $C_1$–$C_8$alkoxycarbonyl, phenoxycarbonyl or benzyloxycarbonyl or 9-fluorenylmethoxycarbonyl.

In a particularly preferred embodiment, $R_1$ and $R_2$ as protective groups are methyl, ethyl, n- or i-propyl, n-, i- or t-butyl; benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(methoxyphenyl)(phenyl)methyl, trityl, tri(methylphenyl)methyl, tri(dimethylphenyl)methyl, tri(methoxyphenyl)methyl, tri(dimethoxyphenyl)methyl; trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl, —($CH_3$)$_2$Si—O—Si($CH_3$)$_2$—, —(i—$C_3H_7$)$_2$Si—O—Si(i—$C_3H_7$)$_2$—; acetyl, propanoyl, butanoyl, pentanoyl, hexanoyl, benzoyl, methylbenzoyl, methoxybenzoyl, chlorobenzoyl and bromobenzoyl;

methyl-, ethyl-, propyl-, butyl-, phenyl-, benzyl-, p-bromo-, p-methoxy- and p-methylphenylsulfonyl; methoxy-, ethoxy-, n- or i-propoxy- or n-, i- or t-butoxycarbonyl, or phenoxycarbonyl, benzyloxycarbonyl, methyl- or methoxy- or chlorophenoxycarbonyl or -benzyloxycarbonyl or 9-fluorenylmethoxycarbonyl.

As a phosphorus-containing radical forming a nucleotide bridge group, $R_2$ can be of the formula

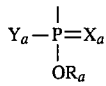

in which $Y_a$ is hydrogen, $C_1$–$C_{12}$alkyl, $C_6$–$C_{12}$aryl, $C_7$–$C_{20}$aralkyl, $C_7$–$C_{20}$alkaaryl, —$OR_b$, —$SR_b$, —$NH_2$, primary amino, secondary amino, $O^\ominus M^\oplus$ or $S^\ominus M^\oplus$; $X_a$ is oxygen or sulfur; $R_a$ is hydrogen, $M^\oplus$, $C_1$–$C_{12}$alkyl, $C_2$–$C_{12}$alkenyl or $C_6$–$C_{12}$aryl, or the group $R_aO$ is N-heteroaryl-N-yl having 5 ring members and 1 to 3 N atoms; $R_b$ is hydrogen, $C_1$–$C_{12}$alkyl or $C_6$–$C_{12}$aryl; and $M^\oplus$ is $Na^\oplus$, $K^\oplus$, $Li^\oplus$, $NH_4^\oplus$ or primary, secondary, tertiary or quaternary ammonium; where alkyl, aryl, aralkyl and alkaryl in $Y_a$, $R_a$ and $R_b$ are unsubstituted or substituted by alkoxy, alkylthio, halogen, —CN, —$NO_2$, phenyl, nitrophenyl or halophenyl.

As primary amino, $Y_a$ preferably contains 1 to 12 and particularly preferably 1 to 6 C atoms, and as secondary amino preferably 2 to 12 and particularly preferably 2 to 6 C atoms.

The primary amino and secondary amino can, for example, be radicals of the formula $R_cR_dN$, in which $R_c$ is H or independently has the meaning of $R_d$, and $R_d$ is $C_1$–$C_{20}$alkyl, -aminoalkyl or -hydroxyalkyl, preferably $C_1$–$C_{12}$alkyl,-aminoalkyl or -hydroxyalkyl and particularly preferably $C_1$–$C_6$alkyl, -aminoalkyl or -hydroxyalkyl; carboxyalkyl or carbalkoxyalkyl, where the carbalkoxy group contains 2 to 8 C atoms and the alkyl group 1 to 6, preferably 1 to 4 C atoms; $C_2$–$C_{20}$alkenyl, preferably $C_2$–$C_{12}$alkenyl and particularly preferably $C_2$–$C_6$alkenyl; phenyl, mono- or di($C_1$–$C_4$alkyl or -alkoxy)phenyl, benzyl, mono- or di($C_1$–$C_4$alkyl- or -alkoxy)benzyl; or 1,2-, 1,3- or 1,4-imidazolyl-$C_1$–$C_6$alkyl, or $R_c$ and $R_d$ together are tetra- or pentamethylene, 3-oxa-1,5-pentylene, —$CH_2$—$NR_e$—$CH_2CH_2$— or —$CH_2CH_2$—$NR_{19}$—$CH_2CH_2$—, in which $R_e$ is H or $C_1$–$C_4$alkyl. The amino group in the aminoalkyl can be substituted by one or two $C_1$–$C_4$alkyl or -hydroxyalkyl groups. The hydroxyl group in the hydroxyalkyl can be etherified with $C_1$–$C_4$alkyl.

For $Y_a$ in connection with the definition of $M^\oplus$, primary, secondary, tertiary and quaternary ammonium are to be understood as meaning an ion of the formula $R_fR_gR_hR_iN^\oplus$, in which $R_f$ is $C_1$–$C_{20}$alkyl, -aminoalkyl or -hydroxyalkyl, preferably $C_1$–$C_{12}$alkyl, -aminoalkyl or -hydroxyalkyl and particularly preferably $C_1$–$C_6$alkyl, -aminoalkyl or -hydroxyalkyl; carboxyalkyl or carbalkoxyalkyl, where the carbalkoxy group contains 2 to 8 C atoms and the alkyl group contains 1 to 6, preferably 1 to 4, C atoms; $C_2$–$C_{20}$alkenyl, preferably $C_2$–$C_{12}$alkenyl and particularly preferably $C_2$–$C_6$alkenyl; phenyl, mono- or di($C_1$–$C_4$alkyl or -alkoxy)phenyl, benzyl, mono- or di($C_1$–$C_4$alkyl or -alkoxy)benzyl; or 1,2-, 1,3- or 1,4-imidazolyl-$C_1$–$C_6$alkyl, and $R_g$, $R_h$ and $R_i$ independently of one another are hydrogen or have the meaning of $R_f$, or $R_f$ and $R_g$ together are tetra- or pentamethylene, 3-oxa-1,5-pentylene, —$CH_2$—$NR_e$—$CH_2CH_2$— or —$CH_2CH_2$—$NR_e$—$CH_2CH_2$—, in which $R_e$ is H or $C_1$–$C_4$alkyl, and $R_h$ and $R_i$ independently of one another have the meaning of $R_f$. The amino group in the aminoalkyl can be substituted by one or two $C_1$–$C_4$alkyl or -hydroxyalkyl groups. The hydroxyl group in the hydroxyalkyl can be etherified with $C_1$–$C_4$alkyl.

Examples of carboxyalkyl are carboxymethyl, carboxyethyl, carboxypropyl and carboxybutyl, and examples of carbalkoxyalkyl are these carboxyalkyl groups esterified with methyl or ethyl. Examples of alkenyl are allyl, but-1-en-3-yl or-4-yl, pent-3- or-4-en-1-yl or -2-yl, hex-3- or -4- or -5-en-1-yl or -2-yl. Examples of alkyl- and alkoxyphenyl or -benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Examples of imidazolylalkyl, in which the alkyl group preferably contains 2 to 4 C atoms, are 1,2-, 1,3- or 1,4-imidazolylethyl or-n-propyl or-n-butyl. $R_{19}$ is preferably H, methyl or ethyl.

Preferred examples of primary amino and secondary amino are methyl-, ethyl-, dimethyl-, diethyl-, di-i-propyl-, mono- or di(1-hydroxyeth-2-yl)-, phenyl- and benzylamino, acetylamino and benzoylamino and piperidinyl, piperazinyl and morpholinyl.

Preferred examples of primary and secondary ammonium are methyl-, ethyl-, dimethyl-, diethyl-, di-i-propyl-, mono- or di(1-hydroxyeth-2-yl)-, phenyl- and benzylammonium.

Examples of $Y_a$, $R_a$ and $R_b$ as alkyl are methyl, ethyl and the isomers of propyl, butyl, pentyl, hexyl, heptyl and octyl; examples of $Y_a$, $R_a$ and $R_b$ as aryl are phenyl and naphthyl; examples of $R_a$ as alkenyl are allyl and ($C_1$–$C_4$alkyl)CH=CH—$CH_2$—; examples of $Y_a$ as aralkyl are phenyl-$C_nH_{2n}$— where n is a number from 1 to 6, particularly benzyl; examples of $Y_a$ as alkaryl are mono-, di- and tri($C_1$–$C_4$-alkyl)phenyl. Preferred substituents are chlorine, bromine, methoxy, —$NO_2$, —CN, 2,4-dichlorophenyl and 4-nitrophenyl. Examples of $R_b$, are 2,2,2-trichloroethyl, 4-chlorophenyl, 2-chlorophenyl and 2,4-dichlorophenyl; and examples of $R_bO$— as N-heteroaryl are pyrrol-N-yl, triazol-N-yl and benzotriazol-N-yl.

In a particularly preferred embodiment, $R_b$ is β-cyanoethyl, $R_a$ is di(i-propylamino) and $X_a$ is O.

If B is a purine radical or an analogue thereof, it can be radicals of the formula II, IIa, IIb, IIc, IId or IIe

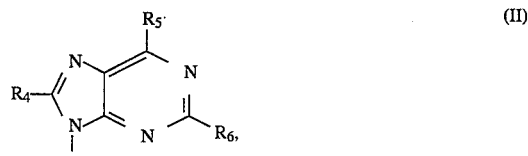

(II)

(IIa)

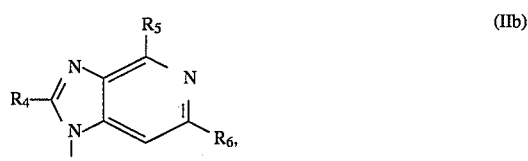

(IIb)

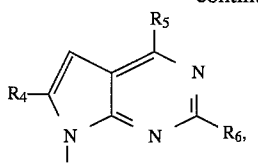

(IIc)

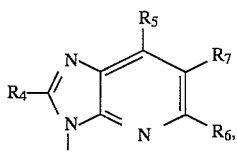

(IId)

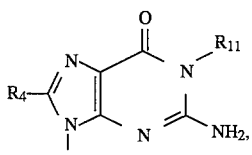

(IIe)

in which $R_4$ is H, Cl, Br, OH or $C_1$–$C_{12}$alkoxy, and $R_5$, $R_6$ and $R_7$ independently of one another are H, OH, SH, $NH_2$, $NHNH_2$, NHOH, NHO alkyl having 1 to 12 C atoms, —N=CH—N($C_1$–$C_{12}$alkyl)$_2$, F, Cl, Br, alkyl or hydroxyalkyl or aminoalkyl or alkoxy or alkylthio having 1 to 12 C atoms, where the hydroxyl and amino groups are unsubstituted or substituted by a protective group, phenyl, benzyl, primary amino having 1 to 20 C atoms or secondary amino having 2 to 30 C atoms, and $R_{11}$ is H or $C_1$–$C_4$alkyl.

Suitable protective groups have been mentioned above. Preferred protective groups are $C_1$–$C_8$acyl groups, for example acetyl, propionyl, butyroyl and benzoyl. $R_{11}$ is preferably H or methyl.

The primary amino preferably contains 1 to 12 and particularly preferably 1 to 6 C atoms, and the secondary amino preferably 2 to 12 and particularly preferably 2 to 6 C atoms.

Some examples of alkyl, alkoxy, alkylthio, hydroxyalkyl and aminoalkyl, which preferably contain 1 to 6 C atoms, are methyl, ethyl and the isomers of propyl, butyl, pentyl, hexyl, heptyl, octyl, nonyl, decyl, undecyl and dodecyl, and also corresponding alkoxy, alkylthio, hydroxyalkyl and aminoalkyl radicals. The alkyl, alkoxy, alkylthio, hydroxyalkyl and aminoalkyl radicals preferably contain 1 to 4 C atoms. Preferred alkyl, alkoxy, alkylthio, hydroxyalkyl and aminoalkyl radicals are methyl, ethyl, n- and i-propyl, n-, i- and t-butyl, methoxy, ethoxy, methylthio and ethylthio, aminomethyl, aminoethyl, hydroxymethyl and hydroxyethyl.

The primary amino and secondary amino can, for example, be radicals of the formula $R_8R_9N$, in which $R_8$ is H or independently has the meaning of $R_9$, and $R_9$ is $C_1$–$C_{20}$alkyl, -aminoalkyl or -hydroxyalkyl, preferably $C_1$–$C_{12}$alkyl, -aminoalkyl or -hydroxyalkyl and particularly preferably $C_1$–$C_6$alkyl, -aminoalkyl or -hydroxyalkyl; carboxyalkyl or carbalkoxyalkyl, where the carbalkoxy group contains 2 to 8 C atoms and the alkyl group contains 1 to 6, preferably 1 to 4, C atoms; $C_2$–$C_{20}$alkenyl, preferably $C_2$–$C_{12}$alkenyl and particularly preferably $C_2$–$C_6$alkenyl; phenyl, mono- or di($C_1$–$C_4$alkyl- or -alkoxy)phenyl, benzyl, mono- or di($C_1$–$C_4$alkyl- or -alkoxy)benzyl; or 1,2-, 1,3- or 1,4-imidazolyl-C$_1$–$C_6$alkyl, or $R_8$ and $R_9$ together are tetra- or pentamethylene, 3-oxa-1,5-pentylene, —CH$_2$—NR$_{10}$—CH$_2$CH$_2$— or —CH$_2$CH$_2$—NR$_{10}$—CH$_2$CH$_2$—, in which $R_{10}$ is H or $C_1$–$C_4$alkyl. The amino group in the aminoalkyl can be substituted by one or two $C_1$–$C_4$alkyl or -hydroxyalkyl groups. The hydroxyl group in hydroxyalkyl can be etherified with $C_1$–$C_4$alkyl.

Examples of alkyl have been given previously. Examples of aminoalkyl are aminomethyl, aminoethyl, 1-aminoprop-2-yl or -3-yl, 1-aminobut-2-yl or -3-yl or-4-yl, N-methyl- or N,N-dimethyl- or N-ethyl- or N,N-diethyl- or N-2-hydroxyethyl- or N,N-di-2-hydroxyethylaminomethyl or -aminoethyl or -aminopropyl or -aminobutyl. Examples of hydroxyalkyl are hydroxymethyl, 1-hydroxyeth-2-yl, 1-hydroxyprop-2- or -3-yl, 1-hydroxybut- 2-yl, -3-yl or -4-yl. Examples of carboxyalkyl are carboxymethyl, carboxyethyl, carboxypropyl and carboxybutyl, and examples of carbalkoxyalkyl are these carboxyalkyl groups esterified with methyl or ethyl. Examples of alkenyl are allyl, but-1-en-3-yl or -4-yl, pent-3- or 4-en-1-yl or -2-yl, hex-3- or -4- or -5-en- 1-yl or -2-yl. Examples of alkyl- and alkoxyphenyl or benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Examples of imidazolylalkyl, in which the alkyl group preferably contains 2 to 4 C atoms, are 1,2-, 1,3- or 1,4-imidazolylethyl or-n-propyl or -n-butyl. $R_{10}$ is preferably H, methyl or ethyl.

Preferred examples of primary amino and secondary amino are methyl-, ethyl-, dimethyl-, diethyl-, allyl-, mono- or di(1-hydroxyeth-2-yl)-, phenyl- and benzylamino, acetylamino, isobutyrylamino and benzoylamino.

In a preferred embodiment, $R_4$ is hydrogen. In another preferred embodiment, $R_7$ is hydrogen. In a further preferred embodiment, $R_5$ and $R_6$ independently of one another are H, F, Cl, Br, OH, SH, $NH_2$, NHOH, $NHNH_2$, methylamino, dimethylamino, benzoylamino, isobutyrylamino, methoxy, ethoxy and methylthio.

Besides purine, some examples of analogues of the purine series are adenine, N-methyladenine, N-benzoyladenine, 2-methylthioadenine, 2-aminoadenine, 6-hydroxypurine, 2-amino-6-chloropurine, 2-amino-6-methylthiopurine, guanine and N-isobutyrylguanine. Adenine, 2-aminoadenine and guanine, and also their base-protected derivatives, are particularly preferred.

If B in formula I is an analogous pyrimidine radical, it is preferably uracil, thymine or cytosine radicals of the formulae III, IIIa and IIIb

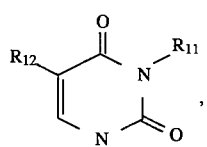

(III)

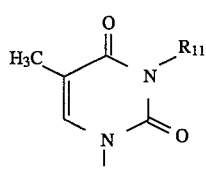

(IIIa)

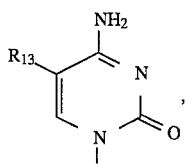

(IIIb)

in which $R_{11}$ is H or $C_1$–$C_4$alkyl, and $R_{12}$ and $R_{13}$ independently of one another have the meaning previously given for $R_5$, including the preferences, and the hydrogen atoms of the $NH_2$ group in formula IIIb can be substituted by $C_1$–$C_6$alkyl or benzoyl, and the dihydro derivatives of the radicals of the formulae II, IIIa and IIIb.

Preferably, $R_{12}$ is H, $C_1$–$C_6$alkyl or hydroxyalkyl, F, Cl, Br, $NH_2$, benzoylamino, mono- or di-$C_1$–$C_6$alkylamino and $R_{13}$ is preferably H, $C_1$–$C_6$alkyl or -alkoxy or -hydroxyalkyl, F, Cl, Br, $NH_2$, benzoylamino, mono- or di-$C_1$–$C_6$alkylamino.

$R_{11}$ is preferably H or methyl. $R_{12}$ is preferably H, F, Cl, Br, $NH_2$, $NHCH_3$, $N(CH_3)_2$ or $C_1$–$C_4$alkyl. $R_{13}$ is preferably H, $C_1$–$C_4$alkyl, preferably methyl, or $NH_2$, $NHCH_3$ or $(CH_3)_2N$.

Some examples of pyrimidine analogues are uracil, thymine, cytosine, 5-fluorouracil, 5-chlorouracil, 5-bromouracil, dihydrouracil and 5-methylcytosine.

Particularly preferred compounds of the formulae I and Ia are those in which $R_1$ and $R_2$ are hydrogen, A is —$CH_2$— and B is thymine, adenine, cytosine or guanine.

The invention further relates to a process for the preparation of compounds of the formula I, which is characterized in that in an enantiomeric compound of the formula IV or IVa or their racemates

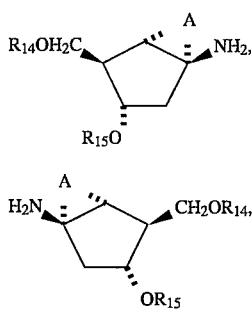

in which A has the meaning given previously, including the preference, and $R_{14}$ and $R_{15}$ are identical or different protective groups, the $NH_2$ group is convened into a radical B in a manner known per se in an inert solvent by synthesis reactions, B being a purine or pyrimidine radical or an analogue thereof.

Synthesis reactions for the radicals B, which are also called nuclein bases, are described in the literature, for example by Y. F. Shealy et at. in J. Heterocyclic Chem., 18:383–389 (1981); M. Arita et al. in J. Am. Chem. Soc., 105:4049–4055 (1983); G. V. B. Madhavan et al. in J. Org. Chem., 51:1287–1293 (1986); V. E. Marquez et al. in J. Med. Chem., 31, pp. 1687–1694 (1988); J. Balzarini et al. in J. Med. Chem., 32:1861–1865 (1989); M. Koga et al. in Tetrahedron Letters, 31:5861–5864 (1990); M. R. Hamden et al. in J. Med. Chem., 33:187–196 (1990) and A. D. Borthwick et al. in Tetrahedron 48:571–623 (1992) [general survey containing further literature references].

Protective groups have been mentioned previously. The temperature in the individual reaction steps of the synthesis reaction can be from −80° to 150° C, preferably 0° to 100° C.

In general, solvents are used which are protic and/or aprotic, and particularly preferably dipolar. Examples of solvents which can be employed on their own or as a mixture of at least two solvents are ethers (dibutyl ether, tetrahydrofuran, dioxane, diethylene glycol dimethyl ether, ethylene glycol dimethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylic acid esters and lactones (ethyl acetate, methyl propionate, ethyl benzoate, 2-methoxyethyl acetate, methoxymethyl acetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoramide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (triethylamine, N-methylpiperidine, N-methylmorpholine), aromatic hydrocarbons, for example benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile), and also aliphatic or cycloaliphatic hydrocarbons (pentane, petroleum ether, hexane, cyclohexane and methylcyclohexane).

The compounds of the formulae IV and IVa having the above substituent definitions are novel and the invention relates to these compounds, together with the compounds of the formulae IV and IVa in which $R_{14}$ and $R_{15}$ are H. The invention thus further relates to the enantiomeric compounds of the formulae IV and IVa and their racemates

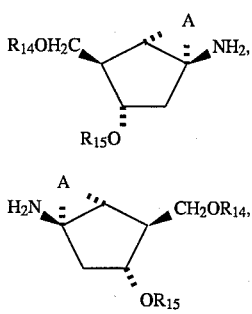

in which A is —$CH_2$— or —$CH_2CH_2$— and $R_{14}$ and $R_{15}$ independently of one another are H or identical or different protective groups. The preferences given previously are valid for A, $R_{14}$ and $R_{15}$. The compounds of the formula IV are preferred.

The compounds of the formulae IV and IVa can be prepared, for example, by the following novel process, to which the invention further relates.

The reaction of the compound described by H.-J Gais et at. in Liebigs Ann. Chem., 1179–1212 (1986), of the formula A

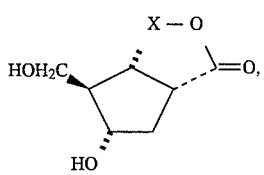

(A)

in which X is the group —CH$_2$, with a trialkylsilyl halide, for example a chloride, bromide or iodide, for example trimethylsilyl chloride or bromide, in alcoholic (for example methanolic) solution, if appropriate in the presence of anhydrous metal halides, for example zinc dichloride or dibromide, leads to compounds of the formula B

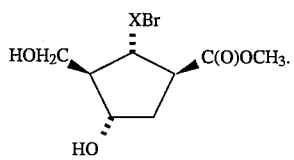

(B)

From the hydroxyl-protected compounds of the formula B, hydroxyl-protected compounds of the formula B' where X is —CH$_2$CH$_2$— can be obtained by converting them, for example into a Grignard compound (for example with magnesium), rearranging this Grignard compound into the corresponding β-hydroxyethyl compound by reaction with formaldehyde and subsequent hydrolysis, and then reacting this hydroxy group with a halogenating reagent, for example HCl, HBr, SOCl$_2$, CCl$_4$/triphenylphosphine or CBr$_4$/triphenylphosphine.

The compounds of the formula B can be convened in a known manner into hydroxyl-protected derivatives of the formula C

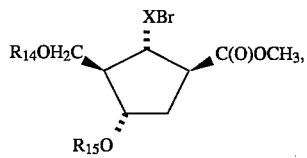

(C)

in which R$_{14}$ and R$_{15}$ are identical or different protective groups or R$_{14}$ and R$_{15}$ together are a protective group, for example t-butyldimethylsilyl, and X is —CH$_2$—. The compounds of the formula C also include the compounds of the formula B' in which X is then —CH$_2$CH$_2$—.

The compounds of the formula C (or B' where X is —CH$_2$—CH$_2$—) can be cyclised by the action of strong bases (for example of alkali metal alkoxides) to the compounds of the formula D

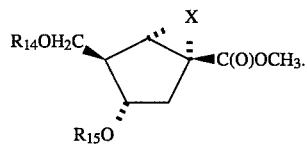

(D)

The compounds of the formula D can then be hydrolysed in a customary manner to the corresponding carboxylic acid, which is then converted into the corresponding carboxylic acid azide (for example using diphenylphosphonyl azide). The carboxylic acid azide is rearranged in the presence of a tertiary amine, for example triethylamine, to the isocyanate (Curtius rearrangement), which is then reacted with a suitable alcohol, for example benzyl alcohol, to give a urethane of the formula E

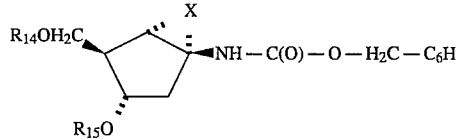

(E)

where X is —CH$_2$— or —CH$_2$CH$_2$—.

From the compounds of the formula E, the compounds of the formulae IV and IVa can be obtained by removal of the amino-protective group —C(O)—O—CH$_2$—C$_6$H$_5$, for example by catalytic hydrogenation with noble metal catalysts, for example palladium. The compounds of the formulae IV and IVa in which R$_{14}$ and R$_{15}$ are H are obtained by removal of the protective groups before or after hydrogenation. The enantiomers of the formulae IV and IVa can be obtained from the racemates, for example by chromatographic separation processes. However, they can also be prepared starring from enantiomers of the formula A, or one of the intermediates B to E can be separated by chromatography and the reaction continued using the enantiomerically pure intermediates.

The protective groups are in general removed in a known manner from the compounds of the formulae I and Ia before further processing thereof or use thereof as pharmaceutical active compounds, compounds being obtained in which R$_1$ and R$_2$ are hydrogen. From these compounds, oligonucleotides can be synthesised which, by virtue of their interaction with nucleic acids, have useful biological activities and can be used as pharmaceutical active ingredients or as diagnostics.

The invention further relates to the use of the compounds of the formulae I and Ia in the form of racemates for the preparation of oligonucleotides which contain identical or different monomer units of compounds of the formulae I and/or Ia or at least one monomer unit of compounds of the formulae I and/or Ia and at least one monomer unit of other natural or synthetic nucleosides, the oligonucleotides containing 2 to 200 monomer units. The oligonucleotides preferably contain 2 to 100, particularly preferably 2 to 50, and especially preferably 2 to 20 monomer units. Oligonucleotides are preferred which contain identical or different and, particularly, different monomer units of compounds of the formulae I and/or Ia. Additionally, monomer units of synthetic or natural nucleosides which are derived from the D-ribose or 2-deoxyribose are also preferably present. The invention further relates to oligonucleotides of the formula V

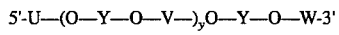

5'-U—(O—Y—O—V—)$_y$O—Y—O—W-3'   (V), in which U, V and W each am identical or different radicals of natural or synthetic nucleosides and at least one of the radicals U, V and/or W is a radical of the formulae VI and/or VIa

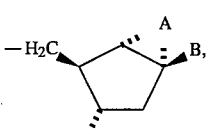

(VI)

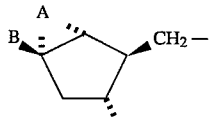

and y is a number from 0 to 200, Y is a nucleotide bridge group, B is a purine or pyrimidine radical or an analogue thereof, and A is —CH$_2$— or —CH$_2$CH$_2$—. The preferences and examples previously given for compounds of the formula I apply to A and B. A preferred bridge group is the group —P(O)O$^\ominus$—, which occurs in natural oligonucleotides. Examples of further bridge groups are —P(O)S$^\ominus$—, —P(S)S$^\ominus$—, —P(O)R$_{16}$—, P(O)NR$_{17}$R$_{18}$, or —CH$_2$—, in which R$_{16}$ is H or C$_1$–C$_6$alkyl and R17 and R$_{18}$ independently of one another have the meaning of R$_{16}$. In formula V, y is preferably a number from 0 to 100, particularly preferably a number from 0 to 50 and especially preferably a number from 0 to 20. The radicals of the formulae VI and/or VIa can be bonded in the end position or in the nucleotide sequence, it being possible for several, for example 2 to 5, radicals of the formulae VI and/or VIa to follow one another, or for the radicals of the formulae VI and/or VIa to be bonded between radicals of natural or synthetic nucleosides, or for mixed forms of these distributions to be present in the nucleotide sequence. Preferably, 4 to 30 nucleoside units are present in all and preferably 1 to 12, particularly preferably 1 to 6 and especially preferably 1 to 4, radicals of the formulae VI and/or VIa are present.

In a preferred embodiment, the oligonucleotide of the formula V contains radicals of the formula VI.

A very particularly preferred embodiment are oligonucleotides of the formula V in which y is a number from 2 to 50, preferably 2 to 30, Y is the group —P(O)O$^\ominus$—, U, V and W each are identical or different radicals of a natural nucleoside and at least one of the radicals U, V or W is of the formulae VI and/or VIa, A is —CH$_2$— and B is the radical of a natural nucleoside base. Possible natural nucleosides are adenosine, cytidine, guanosine, uridine, 2-aminoadenine, 5-methylcytosine, 2'-deoxyadenosine, 2'-deoxycytidine, 2'-deoxyguanosine and thymidine. Natural nucleoside bases which may be particularly mentioned are adenine, cytosine, guanine, thymine and uracil. The radicals of the formulae VI and/or VIa can be bonded in the end position or in the nucleotide sequence, it being possible for several, for example 2 to 5, identical or different radicals of the formulae VI and/or VIa to follow each other, or for identical or different radicals of the formulae VI and/or VIa to be bonded between radicals of natural nucleosides, or for mixed forms of these distributions to be present in the nucleotide sequence. In another preferred embodiment of oligonucleotides of the formula V, all the radicals U, V and W are identical or different radicals of the formulae VI and/or VIa, B being the radical of a natural nucleotide base. y is preferably a number from 2 to 20, and 1 to 12, particularly preferably 1 to 6 and especially preferably 1 to 4, radicals of the formula VIIIb are present in all.

The oligonucleotides according to the invention can be prepared in a manner known per se by various processes in DNA synthesisers which are automated or non-automated and can be purchased together with process instructions. In the case of the bridge group —P(O)O$^\ominus$—, for example, the phosphorus triester process, the phosphite triester process or the H phosphonate process can be used, processes which are familiar to the person skilled in the art. In the phosphite triester process, a procedure can be used, for example, in which the nucleosides of the formula I, in which R$_1$ and R$_2$ are each H, are reacted in the form of their racemates or enantiomers with a protective group reagent, for example 4,4'-dimethoxytriphenylmethyl chloride (abbreviated DMT Cl) to give a nucleoside of the formula F or F' or their racemates

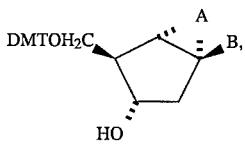

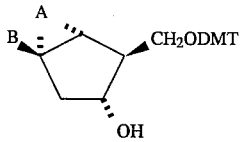

and the compound of the formula F and/or F' is bound with the aid of a "linker", for example succinic anhydride, to a solid support material, for example to controlled pore glass (CPG), which contains long-chain alkylamino groups. In a separate process, the hydroxyl group of the compound of the formula F or F' is derivatised, for example to give a phosphoramidite, by reacting the compound of the formula F or F' using ROP[N(i-propyl)$_2$]$_2$ to give a compound of the formula G and/or G'

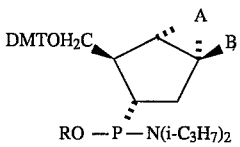

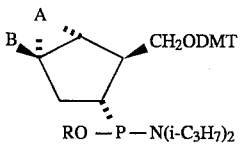

where R is, for example, β-cyanoethyl.

After the removal of the protective group of the material bound to the support, coupling is carried out, with removal of —N(i-C$_3$H$_7$)$_2$, with the compound of the formula G or G', free hydroxyl groups which may be present are blocked (capping) and the phosphite formed is then oxidised to the phosphate. After the deprotection of the dimer, the reaction cycle is repeated with a compound of the formula G or G' until an oligomer having the desired number of monomer units has been synthesised, and the product is detached from the support material. In this way, oligonucleotides are obtained in which all the radicals U, V and W according to formula V consist of radicals of the formulae VI and/or VIa. In this way, oligonucleotides containing any desired monomer units in any desired sequence can also be prepared, depending on the use of synthetic and natural nucleoside components according to the invention in the individual reaction cycles.

The compounds of the formulae I and Ia according to the invention and their racemates in which R$_1$ and R$_2$ are each H have antiviral and antiproliferative properties and can accordingly be used as medicaments. The oligonucleotides according to the invention have a surprisingly high stability to degradation by nucleases. A very good pairing with complementary nucleic acid strands, particularly of the RNA type, is also observed. The oligonucleotides according to the invention are therefore particularly suitable for antisense technology, i.e. for inhibition of the expression of undesired protein products due to the binding to suitable complementary nucleotide sequences in nucleic acids (see EP 0 266 099, WO 87/07300 and WO 89/08146). They can be employed for the treatment of infections and diseases, for example by blocking the expression of bioactive proteins at the nucleic acid stage (for example oncogenes). The oligonucleotides according to the invention are also suitable as diagnostics and can be used as gene probes for the detection of viral infections or of genetically related diseases by selective interaction at the single-or double-stranded nucleic acid stage. In particular—due to the increased stability to nucleases—diagnostic use is not only possible in vitro but also in vivo (for example tissue samples, blood plasma and blood serum). Use possibilities of this type are described, for example, in WO 91/06556.

The invention relates to the use of the oligonucleotides according to the invention as diagnostics for the detection of viral infections or of genetically related diseases.

The invention also relates to the nucleosides of the formulae I and/or Ia according to the invention and the oligonucleotides of the formula V for use in a therapeutic process for the treatment of diseases in mammals including humans by means of inactivation of nucleotide sequences in the body. The dose when administered to mammals of about 70 kg body weight can be, for example, 0.01 to 1000 mg per day. Administration is preferably effected parenterally, for example intravenously or intraperitoneally, in the form of pharmaceutical preparations.

The invention further relates to a pharmaceutical preparation comprising an effective amount of a nucleoside of the formulae I and/or Ia or of an oligonucleotide of the formula V on its own or together with other active ingredients, a pharmaceutical carrier in a customary mount and, if appropriate, excipients.

The pharmacologically active nucleosides and oligonucleotides according to the invention can be used in the form of parenterally administrable preparations or of infusion solutions. Solutions of this type are preferably isotonic aqueous solutions or suspensions, it being possible to prepare these before use, for example in the case of lyophilised preparations which contain the active substance on its own or together with a carrier, for example mannitol. The pharmaceutical preparations can be sterilised and/or contain excipients, for example preservatives, stabilisers, wetting and/or emulsifying agents, solubilisers, salts for regulating the osmotic pressure and/or buffers. The pharmaceutical preparations, which if desired can contain further pharmacologically active substances such as, for example, antibiotics, are prepared in a manner known per se, for example by means of conventional dissolving or lyophilising processes, and contain about 0.1% to 90%, in particular from about 0.5% to about 30%, for example 1% to 5% of active substance(s).

The examples below illustrate the invention. The $^1$H-NMR spectra are based on the numbering of the carbon atoms in the following cyclic carbon skeletons:
Starring compounds:

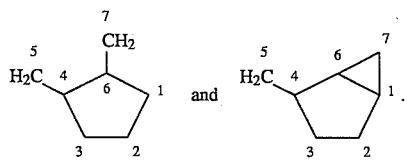

Nucleosides (examples)

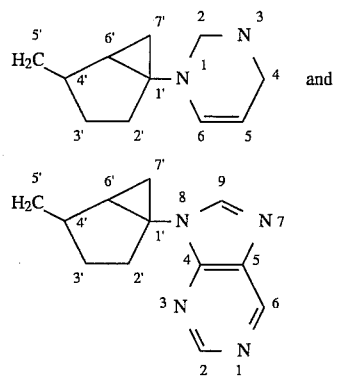

A) Preparation of starring compounds

Example A1:

Preparation of

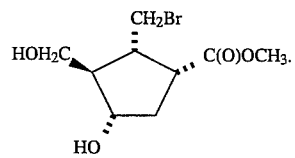

5 ml of trimethylsilyl bromide are added dropwise in the course of 5 min at 0° C. to a solution of 2.0 g (11.6 mmol) of the known compound of the formula A in 50 ml of methanol (MeOH), a spatula tipful of anhydrous $ZnBr_2$ is added and the mixture is then stirred for 18 h at 0° C. The solvent is then removed in a rotary evaporator (bath temperature< 30° C.). The oily residue is dissolved in MeOH, the solvent is removed once more in the rotary evaporator and the process is repeated a further two times. The oil which remains is dried over NaOH in a high vacuum and then purified by flash chromatography on 180 g of silica gel in the eluent system ethyl acetate/methanol (9:1). Yield: 2.16 g (70% ) of viscous brown oil, which starts to decompose at room temperature (RT) within a few days, but can be stored at −20° C. for a relatively long time.

$^1$H-NMR (250 MHz, $CDCl_3$): 4.07 [q, 1H, C(3)$\underline{H}$] 3.68 [s, O$\underline{CH_3}$].

$^{13}$C-NMR (62.9 MHz, $CDCl_3$): 76.34 [C(3)]; 64.10 [C(5)]; 55.04,50.84 [$\underline{C}$H, O$\underline{C}H_3$]

Example A2:

Preparation of

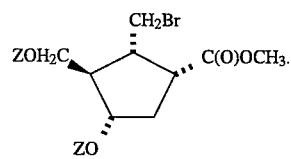

A solution of 4.03 g (15.1 mmol) of compound (2) in 50 ml of dimethylformamide (DMF) is treated dropwise with ice-cooling in the course of 10 min with 9.4 ml (45.3 mmol) of N-tert-butyldimethylsilyl-N-methylacetamide. The ice bath is then removed and the mixture is stirred for 2.5 h at RT. The reaction mixture is diluted in 300 ml of diethyl ether, extracted three times by shaking with 100 ml of ice-water each time and the organic phase is dried and evaporated in a rotary evaporator. The yellow oil which remains is purified on 180 g of silica gel using $CH_2Cl_2$ as the eluent. 4.77 g (64%) of a slightly yellowish-coloured oil are obtained.

$^1$H-NMR (250 MHz, $CDCl_3$): 3.98 [dd, J=18 Hz, J=7 Hz, 1H, C( 3)H]; 3.63[m, 5H, $OCH_3$ und C(5)H2]; 0.80 [s, 18 H, $CH_3$(t-butyl)].

$^{13}$C-NMR (62.9 MHz, $CDCl_3$): 71.73 [C(3)]; 60.65 [C(5)1; 53.18 [C( 4)]; 36.49 [C(2)]; 33.59 [C(7)]; 24.90 [$CH_3$ (tert-butyl)]; 24.76 [$CH_3$(tert-butyl)].

Example A3

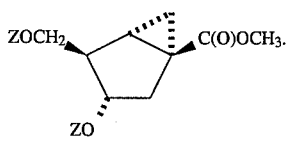

Z = t-butyldimethylsilyl-

A solution of 1.17 g (10.5 mmol) of potassium tert-butoxide is added at RT to a solution of 4.72 g (9.52 mmol) of compound (3) in 30 ml of tert-butanol. The resulting suspension is stirred for 30 min at RT and the reaction mixture is then poured into 300 ml of diethyl ether. It is extracted three times by shaking with 100 ml of ice-water each time, the organic phase is dried and the solvent is removed in a rotary evaporator. Purification on 180 g of silica gel using $CH_2Cl_2/N(C_2H_5)_3$ (99.5:0.5) as the eluent yields 3.03 g (76%) of compound (4) as a colourless oil.

$[\alpha]_D^{20}$=22.85 (c=1.204, $CHCl_3$).

$^1$H-NMR (500 MHz, $CDCl_3$): 4.17 [d, J=6.5 Hz, 1H, C(3) H]; 3.64 [s, 3H, OCH$_3$];3.53[dd,J=10.0Hz,J=5.5Hz,1H,C(5)+e,unsH]; 3.65 [dd, J= 10.0 Hz, J=7.8 Hz, 1H, C(5)H]; 2.50 [ddd, J=14.0 Hz, J=6.5 Hz, J=1.5 Hz, 1H, C(2)H-β; 1.81 [d,J=14.0 Hz, 1H, C(2)H-α]; 1.71 [ddd, J=8.5 Hz, J=5.0 Hz, J<1 Hz, 1H, C( 6) H]; 1.48 [dd,J=5.5 Hz, J=4.0 Hz, 1H, C(7)H-endo]; 1.42 [ddd, J=8.5 Hz, J=4.0 Hz, J= 1.5 Hz, 1H, C(7)H-exo]; 0.89 [s, 9H, $CH_3$ (t-butyl)]; 0.86 [s, 9H, $CH_3$ (t-butyl)].

$^{13}$C-NMR (125.8 MHz, $CDCl_3$): 75.41 [C(3)]; 64.85 [C(5)]; 52.86 [C(4)]; 36.90 [C(2)]; 31.91 [C(6)]; 30.84 [C(1)]; 25.92.

Example A4

Preparation of

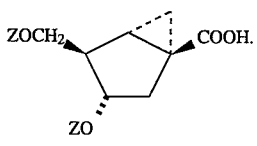

Z = t-butyldimethylsilyl-

1.03g (18.44 mmol) of finely powdered KOH is added with ice-cooling to a solution of 2.18 g (5.26 mmol) of compound (4) in 53 ml of ethanol. The ice-bath is then removed, and the mixture is stirred for 15 min at RT and then heated to reflux for 5 h. The reaction mixture is then evaporated in a rotary evaporator, the residue is treated with 100 ml of diethyl ether and 50 ml of ice-water and the pH of the mixture is adjusted to ~3 with vigorous stirring by addition of 2N HCl (pH electrode). The organic phase is separated off and the aqueous phase is extracted a further three times with 100 ml of ether each time. The combined organic phases am dried mad evaporated in a rotary evaporator. The semi-crystalline residue which remains is purified by flash chromatography on 160 g of silica gel using $CH_2Cl_2$/diethyl ether (4:1) as the eluent. Yield: 1.63 g (78%) of white crystals. M.p. 120.1°–121.6° C.

$[\alpha]_D^{20}$=–27.67 (c=1.095, $CHCl_3$).

$^1$H-NMR (500 MHz, $CDCl_3$): ~11 [s, very broad, 1H, COOH]; 4.16 [d, J=6.2 Hz, 1H, C(3)H]; 3.51 [dd, J=10.0 Hz, J=6.0 Hz, 1H, C(5)H]; 3.32 [dd, J=10.0 Hz, J=8.0 Hz, 1H, C(5)H]; 2.47 [ddd, J=14 Hz, J=6.2 Hz, J~1 Hz, 1H, C( 2) H-β]; 2.07 [dd, J=8.0 Hz, J=6.0 Hz, 1H, C(4)H]; 1.78 [d, J=14 Hz, 1H, C( 2)H-α]; 1.66 [dd, J=9.0 Hz, J=5.6 Hz, 1H, C(6)H]; 1.54 [dd, J=5.6 Hz, J=4.0 Hz, 1H, C( 7)H-endo].

$^{13}$C-NMR (125.8 MHz, $CDCl_3$): 75.36 [C(3)]; 64.78 [C(5)]; 52.87 [C(4)]; 36.37 [C(2)]; 33.24 [C(6)]; 30.72 [C(1)]; 25.96 [$CH_3$ (t-butyl)]; 25.80 [$CH_3$ (t-butyl)].

Example A5

Preparation of

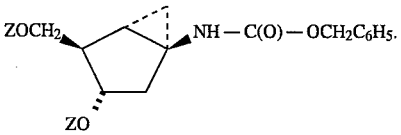

Z = t-butyldimethylsilyl-

882 µl (3.88 mmol) of diphenylphosphoryl azide (95%) and 586 µl (4.24 mmol) of $N(C_2H_5)_3$ are added at 0° C. to a solution of 1.41 g (3.53 mmol) of compound ( 5) in 35 ml of absolute toluene. The solution is stirred at 0° C. for 1 h and at RT for 1.5 h and at 80° C. for 2 h. After cooling to RT, 804 µl (7.77 mmol) of anhydrous benzyl alcohol and a spatula tipful of dibutyltin laurate are added and the solution is stirred at 80° C. for 2 h and then at 100° C. for a further 15 min. The reaction mixture is then cooled to RT, diluted with 100 ml of diethyl ether and extracted twice by shaking with 20 ml of saturated $NaHCO_3$ solution each time and twice by shaking with 100 ml of water each time. After drying over $MgSO_4$, the organic phase is evaporated in a rotary evaporator and the oily residue which remains is purified by flash chromatography on 80 g of silica gel using $CH_2Cl_2$ as the eluent. 1.51 g (85%) of incompletely pure compound (6) are obtained as a viscous oil.

$[\alpha]_D^{20}$=+6.52 (c=1.012, $CHCl_3$).

$^1$H-NMR (500 MHz, $CDCl_3$) (all signals very broad): 4.13 [m, 1H, C(3)H] 3.85 [m, 1H, C(5)H]; 3.57 [m, 1H, C(5) H]; 2.32 [m, 1H, C(2)H-β]; 1.95 [m, 1H, C(4)H]; 1.90 [d, J=14 Hz, 1H, C(2)H-α]; 1.13 [m, 1H, C(6)H+C(7) H-endo].

$^{13}$C-NMR (125.8 MHz, $CDCl_3$) (many signals very broad): 155.93 [C=O (urethane)]; 136.58 [C aromatic]; 128.54 [C aromatic]; 128.10 [C aromatic]; 74.21 [C(3)]; 66.36 [$C_6H_5$—$CH_2$]; 64.63 [C(5)]; 53.41 [C(4)]; 40.42 [C( 1)]; 40.04 [C(2)]; 26.89 [C(6)].

Example A6

Preparation of

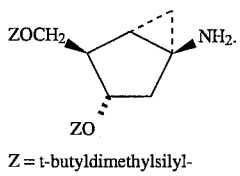
(7)

Z = t-butyldimethylsilyl-

Compound (6) (3.23 g, 6.40 mmol) is dissolved in 65 ml of absolute toluene. After addition of 650 mg of 10% Pd/C, $H_2$ is passed through the mixture for 2 h with vigorous stirring. The catalyst is then removed by filtration and washed with ethyl acetate, and the combined filtrates are extracted three times with 50 ml of saturated $NaHCO_3$ each time. After drying over $MgSO_4$ and removal of the solvent in a rotary evaporator, the colourless liquid which remains is chromatographed in the elution system ethyl acetate/methanol (19:1) to ethyl acetate/methanol (9:1). 870 mg (84%) of the compound (7) are obtained as a colourless oil.

$[\alpha]_D^{20}$ =10.76 (C=1.00, $CHCl_3$)

$^1$H-NMR (500 MHz, $CDCl_3$): 4.10 [dd, J=6.5 Hz, J<1 Hz, 1H, C( 3)H̲]; 3.57 [dd, J=10.0 Hz, J=5.3 Hz, 1H, C(5)H̲]; 3.38 [dd, J=10.0 Hz, J= 8.0 Hz, 1H, C(5)H̲]; 2.02 [ddd, J=13.0 Hz, J=6.5 Hz, J=2.0 Hz, 1H, C(2)H̲-β̲; 1.92 [dd, J= 8.0 Hz, J=5.3 Hz, 1H, C(4)H̲]; 1.89 [d, J=13 Hz, 1H, C(2) H̲-α]; 1.62 [s, broad, 2H, NH̲₂]; 1.11 [dd (tripletoid), J=4.5 Hz, J=4.5 Hz, 1H, C(7)H̲-endo].

$^{13}$C-NMR (125.8 MHz, $CDCl_3$): 74.99 [C(3)]; 65.45 [C(5)]; 53.53 [C(4)]; 44.86 [C(2)]; 42.67 [C(1)]; 27.67 [C(6)]; 18.46 [C(7)]; 26.02 [C̲H₃ (t-butyl)]; 25.81 [C̲H₃ (t-butyl)].

B) Preparation of nucleoside analogues

Example B1

Preparation of

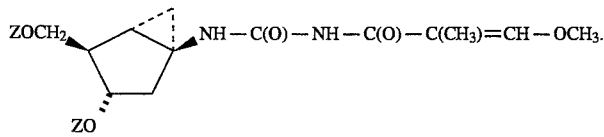
(8)

Z = t-butyldimethylsilyl-

A solution of 770 mg (2.08 mmol) of compound (7) in 10 ml of $CH_2Cl_2$ is cooled to –60° C. and 387 mg (2.70 mmol) of β-methoxy-α-methylacryloyl isocyanate are slowly added dropwise at this temperature. The cooling bath is removed and the mixture is warmed to RT. After standing at RT for 18 hours, the mixture is diluted with diethyl ether, extracted three times by shaking with 20 ml of saturated $NaHCO_3$ solution each time, dried over $MgSO_4$ and evaporated. Flash chromatography on 80 g of silica gel using $CH_2Cl_2$/diethyl ether as the eluent yields 898 mg (85%) of compound (8) as a viscous oil.

$[\alpha]_D^{20}$=–22.69 (c=1.04, $CHCl_3$).

$^1$H-NMR (500 MHz, $CDCl_3$): 8.79 [s, 1H, NH(imide)]; 7.36 [s, 1H, NH(amide)]; 7.30 [d, J=1.1 Hz, 1H, C=CH̲]; 4.20 [dd, J=6.5 Hz, $^4J_{w3,6}$<1 Hz, 1H, C(3)H̲]; 3.67 [dd, J=10.0 Hz, J=5.5 Hz, 1H, C(5)H̲]; 2.40 [ddd, J=13 Hz, J= 6.5 Hz, J=2.0 Hz, 1H, C(2)H̲-β̲]; 2.01 [dd, J=10 Hz, J=5.5 Hz, 1H, C(4)H̲]; 1.95 [d, J=13.0 Hz, 1H, C(2)H̲-α]. $^{13}$C-NMR (125.8 MHz, $CDCl_3$): 169.34 [C=O amide]; 158.49 [=CH(O$CH_3$)]; 154.49 [C=O urea]; 107.11 [=C̲($CH_3$)=].

Example B2

Preparation of

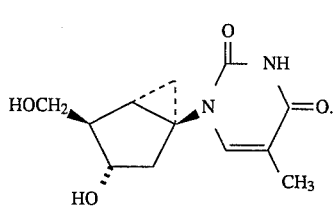
(9)

A solution of 2.57 g (5.02 mmol) of compound (8) in 58 ml of ethanol and 6.46 ml of 2N aqueous HCl is heated to reflux for 10 h. The solvent is then removed in a rotary evaporator and the residual oil is treated three times with ethanol in the rotary evaporator. The foam obtained in this way is dissolved in 10 ml of isopropanol at 40° C. and 10 ml of pentane are added with stirring. After standing at RT for 7 hours and at –20° C. for 2 h, 1.01 g (80%) of crystalline compound (9) are obtained. M.p. 206°–206.4° C.

$^1$H-NMR (500 MHz, DMSO-$d_6$): 11.13 [s, 1H, NH]; 7.46 [d, J=1.2 Hz, 1H, C(6)H̲]; 4.71 [t, J=5.1 Hz, C(5)H₂OH̲]; 4.62 [d, J=3.0 Hz, C(3)HOH̲]; 4.02 [dd, $^3$J=6.5 Hz, $^4J_{w3'6'}$= 2.0 Hz, 1H, C(3)H̲]; 3.50 [m, 2H, C(5)H̲₂]; 2.10 [ddd, $^3J_{2'\beta2'\alpha}$=13 Hz, $^3J_{2'\beta3'}$=6.5 Hz, $^4J_{w2'\beta7'-exo}$=2.0 Hz, 1H, C(2') H-β̲]; 1.92 [d, J=13 Hz, 1H, C(2')H̲-α]; 1.87 [t, J=6 Hz, 1H, C(4')H̲]; 1.72 [d, J=1.2 Hz, 3H, C(5)C̲H₃]; 1.55 [ddd, J=10 Hz, J=5 Hz, J=1 Hz, 1H, C(6')H̲]; 1.33 [dd (tripletoid), J=5 Hz, J=5 Hz, 1H, C( 7')H̲-endo]; 1.00 [ddd, J=10 Hz, J=5 Hz, J=2 Hz, 1H, C(7')H̲-exo].

Example B3

Preparation of

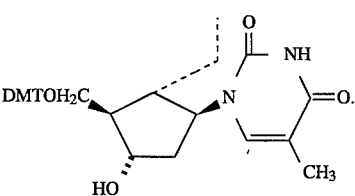
(10)

DMT = 4,4'-dimethoxytrityl 488 mg (1.44 mmol) of 4,4'-dimethoxytrityl chloride, 233 μl (1.68 mmol) of N($C_2H_5$)₃ and a spatula tipful of N,N-dimethyl-4-aminopyridine are added to a solution of 302 mg (1.2 mmol) of compound (9) in 12 ml of absolute pyridine. The reaction mixture is stirred at RT for 3 h and then poured into 50 ml of diethyl ether and 50 ml of ice-water. The organic phase is separated off and the aqueous phase is extracted a further three times with 50 ml of diethyl ether each time. The oil which remains after drying and evaporation of the combined organic extracts is purified by flash $^{31}$P-NMR (CDCl$_3$): 147.80

Example B5

Preparation of

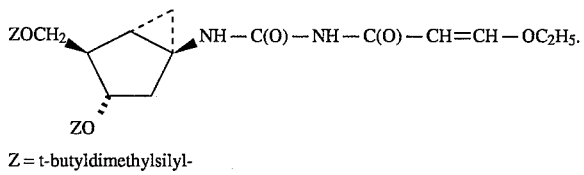

Z = t-butyldimethylsilylchromatography on 80 g of silica gel using ethyl acetate/N(C$_2$H$_5$)$_3$ (99:1). After fresh chromatography on 80 g of silica gel using CH$_2$Cl$_2$/methanol/N(C$_2$H$_5$)$_3$ (19:1:0.02), 542 mg (82%) of the title compound are obtained as a slightly yellowish-coloured foam.

$^1$H-NMR (250 MHz, CDCl$_3$): 8.45 [s, broad, 1H, NH]; 7.45–7.15 [m, 9H, H aromat.]; 7.10 [s, 1H, C(6)H]; 6.82 [d, J=7.5 Hz, 4H, H aromat.]; 4.38 [d, J= 6.5 Hz, 1H C(3')H]; 3.78 s, 6H, OCH$_3$]; 3.49 [dd, J=12.5 Hz, J=5.5 HZ, 1H, C(5')H]; 3.25 [dd, J=12.5 Hz, J=6.5 Hz, 1H, C(5')H]; 2.40–2.10 [m, 3H, C(2')H-α+–β, C(4')H]; 1.79 [s, broad, 1H, OH]; 1.65–1.55 [m, 5H, C(6)—CH$_3$+C(6')H+C(7')H-endo]; 1.12 [m, 1H, C(7')H-exo].

Example B4

Preparation of

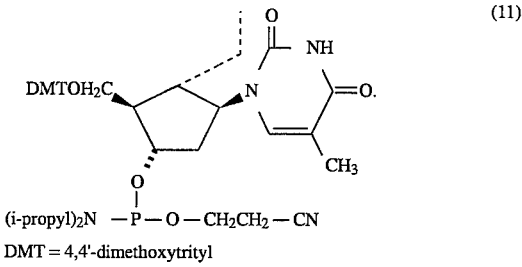

DMT = 4,4'-dimethoxytrityl

A solution of 542 mg (0.98 mmol) of compound (10) in 6 ml of absolute CH$_2$Cl$_2$ is added dropwise in the course of 2 min to a solution of 200 mg (1.17 mmol) of diisopropylammonium tetrazolide and 324 mg (1.08 mmol) of 2-cyanoethoxy-bis(diisopropylamino)phosphine in 6 ml of absolute CH$_2$Cl$_2$. The mixture is stirred at RT for 3 h, then poured into a mixture of 70 ml of saturated NaHCO$_3$ and 70 ml of CH$_2$Cl$_2$, the organic phase is separated off and the aqueous phase is extracted a further three times with 50 ml of CH$_2$Cl$_2$ each time. The combined organic extracts are dried (MgSO$_4$), evaporated in a rotary evaporator and the residue which remains is purified by flash chromatography on 80 g of silica gel [ethyl acetate/toluene/N(C$_2$H$_5$)$_3$ (1:1:0.02)]. The title compound purified in this way is dissolved in 2 ml of absolute CH$_2$Cl$_2$ and this solution is added dropwise with stirring to 80 ml of pentane. After filtration and drying, 544 mg (74%) of compound (11) [diastereomer mixture]are obtained as an amorphous, electrostatically strongly charged white powder.

$^1$H-NMR (500 MHz, CDCl$_3$): 7.45–7.10 [m, 11H]; 6.88–6.78 [m, 4H]; 4.60 [m, broad, 1H, C(3')H]; 3.80–3.58 [m, including singlet at 3.80 (OCH$_3$), 5H]; 3.65–3.60 [m, 2H]; 3.38 [m, 1H]; 3.28 [m, 1H]; 2.60–2.30 [m, 5H]; 1.65–1.50 [m, 5H]; 1.20–1.08 [m, 13H];

A solution of 2.25 g (6.06 mmol) of compound (7) in 20 ml of absolute CH$_2$Cl$_2$ is cooled to −60° C. and 1.11 g (7.88 mmol) of β-ethoxyacryloyl isocyanate are added at this temperature. The cooling bath is then removed and the mixture warmed to RT. After 30 min at RT, it is diluted with diethyl ether, extracted three times by shaking with 50 ml of saturated NaHCO$_3$ each time, and the organic phase is dried and evaporated. Purification of the residue on 100 g of silica gel using CH$_2$Cl$_2$/diethyl ether/N(C$_2$H$_5$)$_3$ (19:1:0.2) yields 2.95 g (95%) of the title compound as a white foam.

$^1$H-NMR (250 MHz, CDCl$_3$) 2 isomers (~10/1), only main isomer indicated; 9.96 [s, 1H, NH (imide)]; 8.86 [s, 1H, NH (amide)]; 7.58 [d, J=12.0 Hz, 1H, =CH—O—]; 5.28 [d, J=12.0 Hz, 1H, (O)C—CH=]; 4.12 [d, J=5.0 Hz, 1H, C(3)H]; 3.90 [m, 2H, C(5')H]; 3.55 [m, 2H, OCH$_2$CH$_3$]; 2.33 [dd, J=13 Hz, J=6.0 Hz, 1H, C( 2')H-β]; 1.93 [m, 2H, C(2)H-α+C(4)H]; 1.40–1.15 [m, 5H, OCH$_2$CH$_3$+C(6)H+C(7)H-endo]; 0.84 (s, broad, CH$_3$ (tert-butyl), overlies C(7)H-exo]; 0.00 [s, broad, Si—CH$_3$].

Example B6

Preparation of

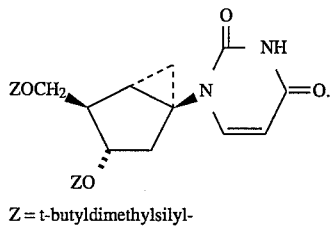

Z = t-butyldimethylsilyl-

A solution of 2.95 g (5.77 mmol) of compound (12) in 104 ml of ethanol and 11.5 ml of 2N aqueous HCl is heated to reflux for 7 h. The solvent is then removed in a rotary evaporator, and the residue which remains is treated four times with ethanol in the rotary evaporator, dried in a high vacuum and then redissolved in 50 ml of DMF. 1.18 g (17.31 mmol) of imidazole and 2.08 g (13.85 mmol) of tert-butyldimethylsilyl chloride and also a spatula tipful of N,N-dimethyl-4-aminopyridine are added to this solution. After stirring at RT for 18 hours, it is diluted with 100 ml of diethyl ether, extracted three times by shaking with 50 ml of ice-water each time, dried over MgSO$_4$ and evaporated. Purification on 200 g of silica gel using diethyl ether as the eluent yields 2.35 g (87%) of the title compound as a white foam.

$^1$H-NMR (250 MHz, CDCl$_3$): 9.43 [s, broad, 1H, NH]; 7.35 [d, J= 8.0 Hz, C(6)H]; 5.57 [d, J=8.0 Hz, 1H, C(5)H]; 4.15 [d, J=5.5 Hz, 1H, C( 3')H]; 3.68 [d, J=4 Hz, 2H, C(5')H$_2$]; 2.24 [m, 1H, C(2')H-β]; 1.97 [m, 2H, C( 2')

H-α+C(4')H]; 1.48 [m, 2H, C(6')H+C( 7')H-endo]; 0.82, 0.78 [2×s, CH₃ (tert-butyl), overlie C(7')H-exo]; 0.00, −0.008 [2×s, Si—CH₃].

Example B7

Preparation of

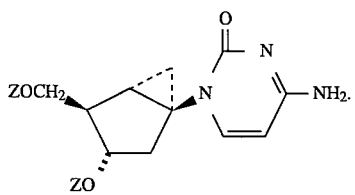

Z = t-butyldimethylsilyl-

891μl (9.76 mmol) of freshly distilled POCl₃ are added dropwise in the course of 10 min to a solution of 1.865 g (4 mmol) of compound (13), 12.8 ml (92.5 mmol) of N(C₂H₅)₃ and 6.22 g (90 mmol) of 1,2,4-triazole in 40 ml of absolute CH₃CN. The mixture is stirred at RT for 1.5 h, then poured into a mixture of 500 ml of CH₂Cl₂, 50 ml of N(C₂H₅)₃ and 150 ml of saturated NaHCO₃, the organic phase is separated off and the aqueous phase is extracted a further two times with 100 ml of CH₂Cl₂ each time. After drying and evaporation of the organic extracts, the residue is filtered through 180 g of silica gel (diethyl ether); the tetrazolide thus obtained (white foam) is dissolved in 48 ml of dioxane, 16 ml of concentrated ammonia are added and the mixture is stirred at 40° C. for 18 h. After removal of the solvent in a rotary evaporator, the residue is partitioned between CH₂Cl₂ and water, the organic phase is separated off and the aqueous phase is extracted a further two times using 100 ml of CH₂Cl₂ each time. After drying and evaporation of the combined organic extracts, the residue which remains is chromatographed on 180 g of silica gel using methanol/ethyl acetate as the eluent. 1.37 g (73%) of the title compound are obtained as an amorphous solid.

¹H-NMR (250 MHz, CDCl₃): 7.31 [d, J=5.5 Hz, 1H, C(6) H]; 5.68 [d, J=5.5 Hz, 1H, C(5)H]; 4.16 [d, J=5.5 Hz, 1H, C(3')H]; 3.72 [m, 2H, C(5')H₂]; 2.33 [dd, J=14.0 Hz, J=6.0 Hz, 1H, C(2')H-β]; 1.99 [dd (tripletoid), J=6.5 Hz, J= 6.5 Hz, J=6.5 Hz, 1H, C(4')H]; 1.92 [d, J=14.0 Hz, C(2')H-α]; 1.40 [m, 2H, C(6')H+C( 7')H-endo]; 0.92 [m, C(7')H-exo]; 0.82, 0.79 [2 overlapping s, CH₃ (tert-butyl)]; 0.00, −0.06 [2 overlapping s, Si— CH₃].

Example B8

Preparation of

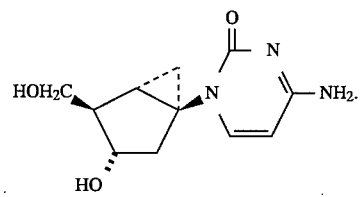

1.71 ml (1.71 mmol) of a 1M solution of tetrabutylammonium fluoride in THF are added to a solution of 200 mg (0.43 mmol) of compound (14) in 5 ml of tetrahydrofuran (THF). After 2 h at RT, the reaction mixture is evaporated in a rotary evaporator and the residue is purified on 180 g of silica gel using ethanol as the eluent. 80 mg of the title compound are thus obtained as a solid which is still slightly contaminated with tetrabutylammonium fluoride. Recrystallisation from 5 ml of isopropanol yields 52.2 mg (51%) of pure compound (15).

¹H-NMR (250 MHz, CDCl₃): 7.61 [d, J=7.5, 1H, C(6) H]; 5.80 [d, J=7.5 Hz, 1H, C(5)H]; 4.20 [d, J=7.0 Hz, C(3') H]; 3.77 [dd, J= 11.0 Hz, J=4.0 Hz, 1H, C(5')H]; 3.64 [J=11.0 Hz, J=4.5 Hz, 1H, C(5')H]; 2.37 [ddd, J= 13.5 Hz, J=7.0 Hz, J=2.5 Hz, 1H, C(2')H-β]; 2.03 [dd (tripletoid), J=4.5 Hz, J=4.5 Hz, 1H, C(4')H]; 1.98 [d, J=13.5 Hz, 1H, C(2')H-α]; 1.65 [ddd, J=9.5 Hz, J=5.0 Hz, J~1 Hz, 1H, C(6') H]; 1.40 [dd (tripletoid), J=5.0 Hz, J=5.0 Hz, 1H, C(7') H-endo]; 1.05 [ddd, J=9.5 Hz, J=5.0 Hz, J=2.5 Hz, 1H, C(7') H-exo].

Example B9

Preparation of

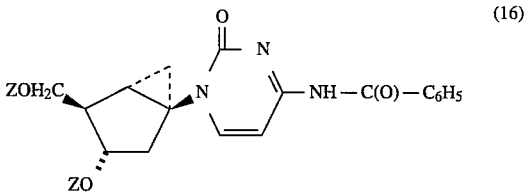

Z = t-butyldimethylsilyl-

188μl (1.62 mmol) of benzoyl chloride are added dropwise to a solution of 630 mg (1.35 mmol) of compound (15) and 279 μl (2.02 mmol) of (C₂H₅)₃N in 20 ml of absolute diethyl ether and a spatula tipful of N,N-dimethyl-4-aminopyridine is then added. After stirring at RT for 1 h, 1 ml of methanol is added and the reaction mixture is poured into a mixture of 50 ml of diethyl ether and 20 ml of saturated NaHCO₃. The organic phase is separated off, washed twice with 20 ml of H₂O each time, dried and evaporated. Filtration through 80 g of silica gel first using CH₂Cl₂ (2 fractions of 80 ml) and then using diethyl ether as the eluent yields 729 mg (95%) of the title compound as a white foam.

¹H-NMR (250 MHz, CDCl₃): 9.05 [very broad, NH]; 7.90–7.80 [m, 3H, 2H aromat.+C(6)H]; 7.60–7.30 [m, 4H, 3H aromat.+C(5)H]; 4.23 [d, J= 5.5 Hz, 1H, C(3')H]; 3.78 [m, 2H, C(5')H₂]; 2.40 [dd,J=12.5 Hz, J=6.5 Hz, 1H, C(2') H-β]; 2.08 [m, 1H, C(2')H-α+C(4')H]; 1.61 [dd (tripletoid), J=5.0 Hz, J=5.0 Hz, 1H, C( 6')H]; 1.53 [dd, J=9 Hz, J=5.0 Hz, 1H, C(7')H-endo]; 1.10 [m, 1H, C(7')H-exo]; 0.88, 0.84 [2×s, CH₃ (tert-butyl)]; 0.08, 0.00 [2×s, Si—CH₃].

Example B10

Preparation of

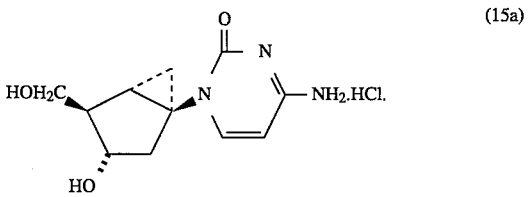

A solution of 653 mg (1.11 mmol) of compound (16) in 18 ml of ethanol and 2 ml of 2N HCl is heated to reflux for 2 h. The solvent is then stripped off in a rotary evaporator, the residue is treated three times with ethanol in the rotary evaporator and then dissolved in 30 ml of hot methanol, very little diethyl ether is added and the mixture is allowed to stand at RT for 2 days. In this way, 224 mg (72%) of the hydrochloride of compound (15) are obtained as a crystalline solid (removal of all protective groups).

$^1$H-NMR (250 MHz, D$_2$O): 8.03 [d, J=7.0 Hz, 1H, C(6)H]; 6.23 [d, J=7.0 Hz, 1H, C(5)H]; 4.37 [d, J=5.5 Hz, 1H, C(3')H]; 3.82 [d, J=4.0 Hz, 2H, C(5')H$_2$]; 2.55 [dd, J=13.5 Hz, J=7.0 Hz, 1H, C(2')H-β]; 2.23 ["t", 2H, C(2')H-α+C(4')H]; 1.98 [dd, J=10.0 Hz, J=4.0 Hz, 1H, C(6')H]; 1.50 [dd (tripletoid), J= 7.0 Hz, J=7.0 Hz, 1H, C(7')H-endo]; 1.42 [m, 1H, C(7')H-exo].

Example B11

Preparation of

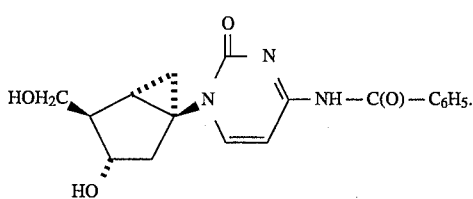

(17)

5.12 ml (5.12 mmol) of a 1M solution of tetrabutylammonium fluoride (TBAF) in THF are added to a solution of 729 mg (1.28 mmol) of compound (16) in 20 ml of THF. After 18 h at RT, a further 5.12 ml of the TBAF solution are added, and after a total of 20 h at RT the mixture is heated at 40° C. for a further 1 h. The solvent is then removed in a rotary evaporator and the residue is purified by flash chromatography on 180 g of silica gel using ethyl acetate/methanol as the eluent. The product-containing fractions are evaporated to dryness and the residue is recrystallised from 10 ml of isopropanol. 230 mg of the pure title compound are thus obtained. The residue obtained after evaporation of the mother liquor is again flash-chromatographed on 80 g of silica gel (ethyl acetate/methanol 4:1). The product-containing fractions are again combined and evaporated. The residue is taken up in 1 ml of isopropanol and, after addition of 5 ml of ether and a seed crystal, the mixture is cooled to 0° C. for 15 min. Filtration additionally yields 116 mg of (17). Total yield: 346 mg (79%).

$^1$H-NMR (250 MHz, CD$_3$OD/D$_2$O): 8.19 [d, J=6.0 Hz, 1H, C(6)H]; 7.97 [d, J=6.0 Hz, 2H, H aromat.]; 7.65–7.45 [m, 4H, 3H aromat.+C(5)H]; 4.30 [d, J=5.5 Hz, 1H, C(3')H]; 3.85 [dd, J=11.0 Hz, J=4.0 Hz, 1H, C(5')H]; 3.77 [dd, J=11.0 Hz, J=5.5 Hz, 1H, C(5')H]; 2.52 [ddd, J=13 Hz, J=6.5 Hz, J~2 Hz, 1H, C(2')H-β]; 2.15 [m, 2H, C(2')H-α+C(4')H]; 1.80 [dd, J=16.5 Hz, J=4.0 Hz, 1H, C(6')H]; 1.59 [dd (tripletoid), J=5.0 Hz, J=5.0 Hz, 1H, C(7')H-endo]; 1.23 [m, 1H, C(7')H-exo].

Example B12

Preparation of

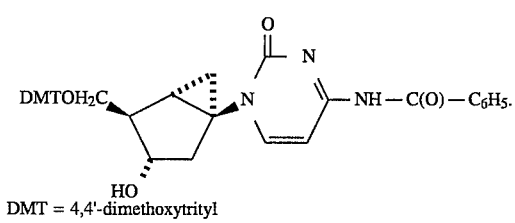

(18)

DMT = 4,4'-dimethoxytrityl

Analogously to Example B3, 563 mg (88%) of the title compound are obtained as a very slightly pale yellow-coloured foam from 346 mg (1.01 mmol) of compound (17) and 410 mg (1.21 mmol) of 4,4'-dimethoxytrityl chloride.

$^1$H-NMR (250 MHz, CDCl$_3$): 8.95 (very broad, NH); 7.90 [d, J=7.5 Hz, 2H, H aromat. o to CONH]; 7.60–7.15 [m, 14H]; 6.85 [d, J=9.0 Hz, 4H, H aromat. o to OCH$_3$]; 4.35 [d, J=5.5 Hz, 1H, C(3')H]; 3.80 [s, 6H, OCH$_3$]; 3.40–3.10 [m, 3H, C(5')H$_2$+OH]; 2.49 [d,J=13.5Hz, 1H]; 2.35–2.15 [m, 2H]; 1.80–1.65 [m, 2H]; 1.11 [m, 1H].

Example B13

Preparation of

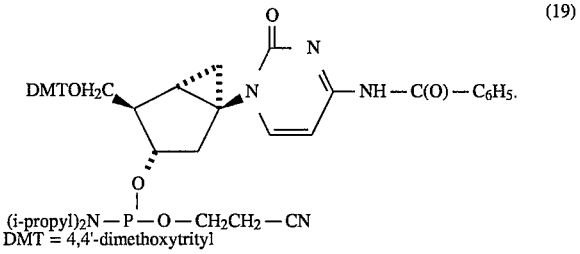

(19)

(i-propyl)$_2$N—P—O—CH$_2$CH$_2$—CN
DMT = 4,4'-dimethoxytrityl

Analogously to Example B4, 646 mg (86%) of the title compound are obtained as a diastereomer mixture from 563 mg (0.876 mmol) of compound (18) and 291 mg (0.964 mmol) of 2-cyanoethoxy-bis(diisopropylamino)phosphine.

$^1$H-NMR (250 MHz, CDCl$_3$): 8.60 (very broad, NH); 7.89 [d, J=7.0 Hz, 2H, H aromat. o to CONH]; 7.60–7.20 [m, 14H]; 6.86 [d, J=8.0 Hz, 4H, H aromat. o to OCH$_3$]; 4.20 [m, broad, 1H, C(3')H]; 3.85–3.65, [m including s at 3.81 (OCH$_3$), 8H]; 3.65–3.45 [m, 2H]3.45–3.25 [m, 2H]; 2.65–2.25 [m, 5H]; 1.62–1.58 [m, 2H]; 1.21–1.10 [m, 13H].

$^{31}$P-NMR (CDCl$_3$): 147.80; 147.72.

Example B14

Preparation of

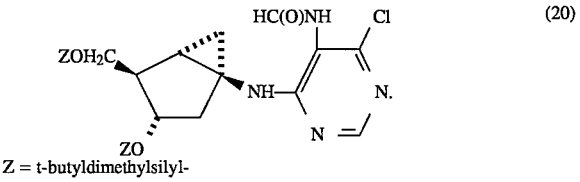

(20)

Z = t-butyldimethylsilyl- 2.42 ml (17.46 mmol) of absolute N(C$_2$H$_5$)$_3$, 1.22 g (6.40 mmol) of 5-formamido-4,6-dichloropyrimidine and 1 spatula tipful of N,N-dimethyl-4-aminopyridine are added to a solution of 2.16 g (5.82 mmol) of compound (7) in 50 ml of absolute dioxane. The mixture is stirred at 50° C. for 18 h, the yellowish suspension is diluted with diethyl ether and filtered, and the filtrate is evaporated. Hash chromatography on 180 g of silica gel [CH$_2$Cl$_2$/ethyl acetate/N(C$_2$H$_5$)$_3$ (4:1:0.05)] and fresh chromatography of the mixed fractions obtained on 80 g of silica gel using the same eluent yield a total of 2.62 g (85%) of the title compound as a virtually white foam.

$^1$H-NMR (250 MHz, CDCl$_3$) (2 rotational isomers): 8.30 (s, main isomer), 8.24 (s, additional isomer), 8.20 (s, main isomer), 7,97 (d, broad, additional isomer), [2H, C(2)H+CHO]; 7.00 (s, broad, main isomer), 6.67 (d, broad, additional isomer); [1H, NH—CHO]; 5.80 [s, broad, NH]; 4.13 [d, J=5.5 Hz, 1H, C(3')H]; 3.78 [dd, J= 18 Hz, J=9 Hz, 1H, C(5')H]; 3.74 [dd, broad, 1H, C(5')H]; 3.63 [dd, J=10 Hz, J= 5.5 Hz, 1H, C(5')H]; 2.45 [m, broad, 1H, C(2')H-β]; 1.98 [m, C(4')H]; 1.82 [d, J= 12 Hz, 1H, C(2')H-α]; 1.40–1.12 [m, C(6')H+C(7')H-endo]; 0.82, 0.79 [ 2 overlapping s, CH₃ (tert-butyl) overlie resonance for C(7')H-exo]; 0.00 [s, 6H, 2×Si—CH₃]; −0.05 [ 2 overlapping s, 6H, Si—CH₃].

Example B15

Preparation of

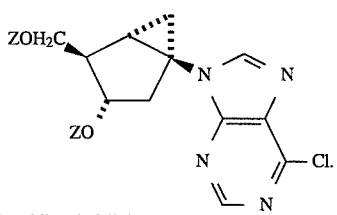

Z = t-butyldimethylsilyl-

A solution of 1.25 g (2.38 mmol) of compound (20) in 12.5 ml of diethoxymethyl acetate is heated at 130° C. for 18 h. The solvent is then removed in a rotary evaporator and the residue which remains is treated with a mixture of 48 ml of methanol and 4 ml of concentrated aqueous ammonia for 30 min. The residue obtained after evaporation of this mixture is dissolved in 100 ml of diethyl ether, the solution is extracted 2×with 50 ml of saturated NaHCO₃ solution each time, dried and evaporated, and the residue which remains is chromatographed on 80 g of silica gel using CH₂Cl₂/ethyl acetate/N(C₂H₅)₃ (4:1:0.05). After fresh chromatography on 180 g of silica gel in the same elution system, 750 mg of compound (21) (62%) are obtained as an amorphous solid.

¹H-NMR (250 MHz, CDCl₃): 8.68 [s, 1H, C(2)H]; 8.15 [s, 1H, C(8)H]; 4.30 [d, J=5.5 Hz, 1H, C(3')H]; 3.88 [m, 2H, C(5')H₂]; 2.52 [ddd, J= 14.0 Hz, J=5.5 Hz, J<1 Hz, 1H, C(2') H-β]; 2.19 [d, J=14.0 Hz, overlapping with m, 2H, C( 2') H-α+C(4')H]; 1.75 [m, 2H, C(6')H+C(7')H-endo]; 1.33 [m, 1H, C(7')H-exo]; 0.89 [s, 9H, CH₃ (tert-butyl)]; 0.85 [s, 9H, CH₃ (tert-butyl)]; 0.08 [2 overlapping s, 2×Si— CH₃; 0.00 [2 overlapping s, 2× Si—CH₃].

Example B16

Preparation of

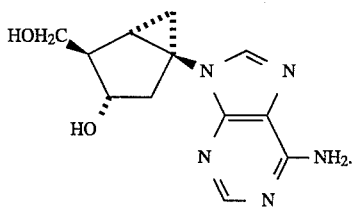

Gaseous ammonia is condensed into a solution of 1.69 g (3.31 mmol) of compound (21) in 20 ml of methanol at −78° C. in a Fischer-Porter apparatus until the volume of the mixture has approximately doubled. The tube is then sealed, warmed to RT and the reaction mixture is stirred at 60° C. for 20 h. The vessel is opened at 0° C., the ammonia is evaporated at RT and normal pressure and the solution which remains is evaporated in a rotary evaporator. The solid residue which remains is dissolved in 20 ml of absolute THF, 20 ml of a 1M solution of tetrabutylammonium fluoride in THF are added and the mixture is then stirred at 60° C. for 3 h. 20 g of ion exchanger (Levatit S 108061/H⁺ form), 20 ml of methanol and 1 ml of water are added and the mixture is stirred at 60° C. for 2 h. The ion exchanger is filtered off, washed three times with MeOH and then suspended in 50 ml of methanol. The mixture is rendered alkaline by addition of concentrated aqueous ammonia, briefly heated to reflux and the ion exchanger is filtered off hot. It is then suspended a further two times in hot methanol and filtered. The combined filtrates are evaporated in the rotary evaporator and the solid residue is suspended in 10 ml of ethanol. Filtration yields 671 mg (78%) of the title compound as white crystals.

¹H-NMR (500 MHz, DMSO-d₆): 8.136, 8.126 [2×s, C(2) H+C(8)H]; 7.24 [s, broad, 2H, NH₂]; 5.22 [dd, J=7.0 Hz, J=4.5 Hz, 1H, CH₂OH]; 4.76 [d, 1H, J=3 Hz, 1 H, CHO H]; 4.16 [d, broad, J=6 Hz, 1H, C(3')H]; 3.70 [ddd (quintethoid), J= 11 Hz, J=6.5 Hz, J=6.5 Hz, 1H, C(5')H]; 2.42 [ddd, J=13.0 Hz, J=6.5 Hz, J= 1.5 Hz, 1H, C(2')H-β]; 2.11 [d, J=13.0 Hz, 1H, C(2')H-α]; 2.02 [dd (tripletoid), J=5.5 Hz, J= 5.5 Hz, 1H, C(4')H]; 1.73 [ddd, J=9 Hz, J=4.5 Hz, J~1 Hz, 1H, C(6')H]; 1.53 [dd (tripletoid), J= 4.5 Hz, J=4.5 Hz, 1H, C(7')H-endo]; 1.30 [ddd, J=9 Hz, J=4.5 Hz, J~ 2 Hz, 1H, C(7')H-exo].

Example B17

Preparation of

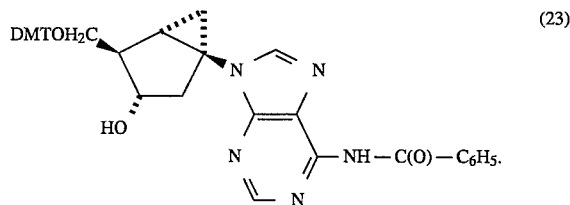

DMT = 4,4'-dimethoxytrityl

951 μl (7.5 mmol) of trimethylchlorosilane are added at 0° C. to a suspension of 392 mg (1.5 mmol) of compound (22) in 14 ml of absolute pyridine. After stirring at 0° C. for 30 min, 871 μl (7.5 mmol) of benzoyl chloride are added dropwise, also at 0° C., the mixture is allowed to warm to RT after removal of the cooling bath and stirred at RT for a further 2 h, and then 3 ml of ice-water are allowed to drip in at 0° C. in the course of 5 min. After 15 min at 0° C., 3 ml of concentrated aqueous ammonia are added dropwise, and the mixture is stirred at RT for 30 min and then evaporated in a rotary evaporator. The solid residue thus obtained is dissolved in 50 ml of water, the solution is extracted by shaking with 50 ml of diethyl ether and the aqueous phase is evaporated again. Purification on 80 g of silica gel using ethyl acetate/methanol as the eluent yields the N⁶-benzoyl derivative of compound (22), which is still contaminated with benzamide and is employed as such in the next step.

¹H-NMR (250 MHz, CD₃OD): u.a. 8.40, 8.18 [2×s, 2×1H, C( 2)H+C(8)H]; 7.35–7.05 [m, aromat. H]; 4.10 [d, J=6.5 Hz, 1H, C(3')H]; 3.69 [dd, J= 11.0 Hz, J=5.0 Hz, 1H, C(5')H]; 3.59 [dd, J=11.0 Hz, J=5.5 Hz, 1H, C(5')H]; 2.30 [m, 1H, C(2')H-β]; 2.01 [d, J=13.5 Hz, 1H, C(2')H-α]; 1.92 [dd (tripletoid), J=5.0 Hz, J= 5.0 Hz, 1H, C(4')H]; 1.62 [m, 1H, C(6')H]; 1.42 [dd (tripletoid), J=6.0 Hz, J=6.0 Hz, 1H, C(7')H-endo]; 1.19 [m, 1H, C(7')H-exo].

The crude product obtained is dissolved in 20 ml of absolute pyridine, 291 μl (2.1 mmol) of N(C₂H₅)₃, 610 mg (1.8 mmol) of 4,4-dimethoxytrityl chloride and a spatula tipful of N,N-dimethyl-4-aminopyridine are added and the solution stirred at RT for 18 h. The mixture is then poured into 50 ml of water and 50 ml of diethyl ether, the organic phase is separated off and the aqueous phase is extracted a further three times using 50 ml of diethyl ether each time.

The combined organic extracts are dried over MgSO₄ and evaporated, and the residue is flash-chromatographed on 80 g of silica gel using ethyl acetate and a little N(C₂H₅)₃. 532 mg (53% based on (22)) of the title compound are obtained as a white foam.

¹H-NMR (250 MHz, CDCl₃): 9.58 [s, broad, 1H, NH]; 8.59 [s, 1H]; 8.04 [d, J=7.5 Hz, 2H, H aromat. o to CONH]; 7.88 [s, 1H]; 7.60–7.18 [m, 12H]; 6.83 [d, J=7.0 Hz, 4H, H aromat. o to OCH₃]; 4.45 [d, J=5.5 Hz, C(3')H]; 3.78 [s, broad, 7H, OCH₃+OH]; 3.44 [m, 2H, C(5')H₂]; 2.55–2.32 [m, 2H]; 2.22 [d, J=13.0 Hz, 1H]; 1.90–1.70 [m, 2H, 1.36 [m, 1H].

Example B18

Preparation of

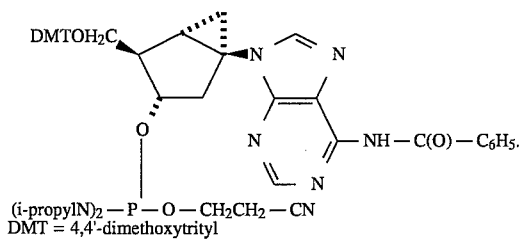

(i-propylN)₂—P—O—CH₂CH₂—CN
DMT = 4,4'-dimethoxytrityl

Analogously to Example B4, 529 mg (79%) of the title compound (diastereomer mixture) are obtained as a strongly electrostatically charged white powder from 530 mg (0.797 mmol) of compound (23) and 264 mg (0.877 mmol) of β-cyanoethoxy-bis(diisopropylamino)phosphine.

¹H-NMR (250 MHz, CDCl₃): 9.25 [s, 1H, NH]; 8.58 [2 overlapping s, 1H, C(2)H]; 8.00 [d, 2H, H aromat. o to CONH]; 7.90 [2 overlapping s, 1H, C(8)H]; 7.60–7.15 [m, H aromat.]; 6.85 [m, 4H, H aromat. o to OCH₃]; 4.50 [m, 1H, C(3')H]; 3.85–3.40 [m incl. s at 3.78 (OCH₃), 12H]; 2.65–2.30 [m, 6H (incl. CH₃ from incompletely removed toluene]; 1.82 [m, 1H]; 1.72 [m, 1H]; 1.42 [m, 1H]; 1.35–1.10 [m, CH₃ (isopropyl)].

³¹P-NMR (CDCl₃): 148.26; 148.10.

Example B19

Preparation of

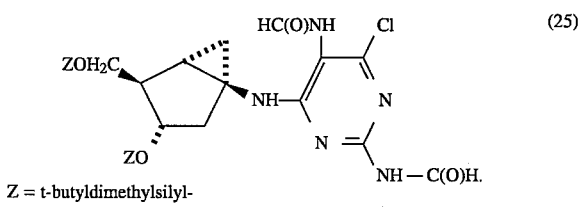

Z = t-butyldimethylsilyl- 3.35ml (24.2 mmol) of absolute N(C₂H₅)₃ and 1.49 g (6.35 mmol) of 2,5-bis(formamido)- 4,6-dichloropyrimidine are added to a solution of 2.25 g (6.05 mmol) of compound (7) in 50 ml of dioxane. The mixture is heated to reflux for 1.5 h, then cooled to 0° C. and diluted with 50 ml of diethyl ether, the solution is filtered and the filtrate is evaporated. The residue is flash-chromatographed on 180 g of silica gel using ethyl acetate. 2.0 g of the title compound are thus obtained as a white foam. Fresh chromatography of the mixed fractions obtained in the first chromatography yields a further 820 mg of compound (25). Total yield: 2.82 g (82%).

¹H-NMR (250 MHz, CD₃OD): 9.30 [s, broad, 1H, C HO]; 8.12 [s, broad, 1H, CHO]; 4.14 [d, J=4.0 Hz, 1H, C(3') H]; 3.63 [dd, J=9.5 Hz, J=6.0 Hz, 1H, C(5')H]; 3.46 [dd (tripletoid), J=9.5 Hz, J=9.5 Hz, 1H, C(5')H]; 2.12 [m, 1H, C( 2')H-β]; 2.06 [d, J=12.0 Hz, 1H, C(2')H-α]; 1.93 [dd, J=9.5 Hz, J=4.0 Hz, 1H, C( 4')H]; 1.36 [m, 2H, C(6') H+C( 7')H-endo]; 0.83 [2 overlapping s, CH₃ (tert-butyl), +C(7')H-exo]; 0.00 [2 overlapping s, Si—CH₃].

Example B20

Preparation of

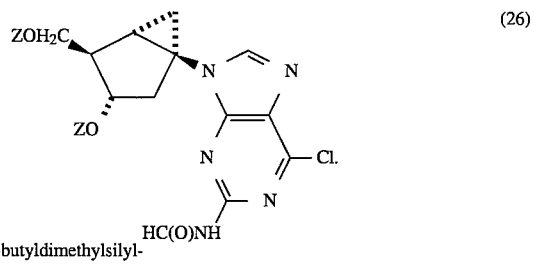

Z = t-butyldimethylsilyl-

A solution of 2.80 g (4.91 mmol) of compound (25) in 25 ml of diethoxymethyl acetate is stirred at 140° C. for 19 h. The solvent is then removed in a rotary evaporator, the residue is dissolved in 18 ml of methanol, 1.5 ml of concentrated aqueous ammonia am added and the mixture is stirred at RT for 30 min. It is then evaporated in a rotary evaporator, the residue is dissolved in 100 ml of ethyl acetate, the solution is extracted twice by shaking with 50 ml of H₂O, and the organic phase is dried and evaporated. The residue is flash-chromatographed on 180 g of silica gel using CH₂Cl₂/ethyl acetate/N(C₂H₅)₃ (9:1:0.1). 1.32 g of the title compound are obtained as an amorphous solid. Fresh chromatography of the product-containing mixed fractions obtained in the first chromatography yields a further 270 mg of (26), which corresponds to a total yield of 59%.

¹H-NMR (250 MHz, CDCl₃): 9.38 [d, J=11.5 Hz, 1H, C HO]; 8.30 [d, J= 11.5 Hz, 1H, NH]; 7.97 [s, 1H, C(8)H]; 4.18 [d, J=5.0 Hz, 1H, C( 3')H]; 3.72 [m, 2H, C(5')H]; 2.38 [ddd, J=13 Hz, J=6.0 Hz, J~1 Hz, 1H, C(2')H-β]; 2.15–2.00 [m, 2H, C(2')H-α+C( 4')H]; 1.73–1.60 [m, 2H, C(6')H+C(7') H-endo]; 1.18 m, 1H, C(7')H-exo]; 0.79, 0.77 [2 overlapping s, CH₃ (tert-butyl)]; 0.00 [s, 6H, Si—CH₃ ]; –0.08 [2 overlapping s, 6H, Si—CH₃].

Example B21

Preparation of

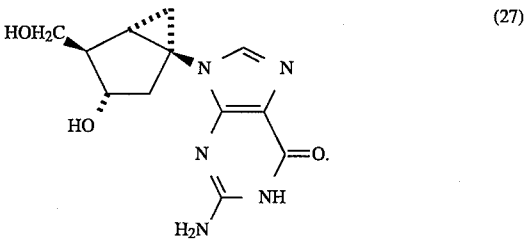

A solution of 1.59 g (2.88 mmol) of compound (26) in 20 ml of 80% strength formic acid is heated to reflux for 1 h. The solvent is then removed in a rotary evaporator, the residue is treated with 20 ml of concentrated aqueous ammonia and 10 ml of methanol and the mixture is stirred at 40° C. for 1 h. The solution is evaporated and the residue is chromatographed on 120 g of silica gel using methanol as the eluent. The solid thus obtained is dissolved in 50 ml of methanol, 3 ml of $N(C_2H_5)_3$ are added and the mixture is stirred at RT for 30 min. The resulting precipitate is filtered off, suspended in 10 ml of aqueous isopropanol (50%), filtered again, washed with isopropanol and diethyl ether and dried in a high vacuum. 705 mg (88%) of the title compound are obtained as a white powder.

$^1$H-NMR (500 MHz, DMSO): 8.49 [s, 1H, N$\underline{H}$]; 7.62 [s, 1H, C(8)$\underline{H}$]; 6.50 [s, broad, 2H, N$\underline{H}_2$]; 4.90 [s, broad, 1H, O$\underline{H}$]; 4.71 [s, broad, 1H, OH]; 4.09 [d, J=5.5 Hz, 1H, C(3')$\underline{H}$]; 3.58 [d, J=4.5 Hz, 2H, C(5')$\underline{H}_2$]; 2.24 [ddd, J= 10.5 Hz, J=5.5 Hz, J=1Hz, 1H, C(2')$\underline{H}$-β]; 2.09 [d, J=10.5 Hz, 1H, C(2')H-α]; 1.96 [dd (tripletoid), J=4.5 Hz, J=4.5 Hz, 1H, C(4')$\underline{H}$]; 1.71 [dd, J=7 Hz, J=3.5 Hz, 1H, C( 6')$\underline{H}$]; 1.46 [dd (tripletoid); J=3.5 Hz, J=3.5 Hz, 1H, C(7')$\underline{H}$-endo]; 1,14 [ddd, J=7 Hz, J= 3.5 Hz, J=1.2 Hz, 1H, C(7')$\underline{H}$-exo].

Example B22

Preparation of

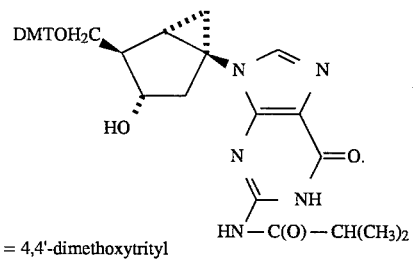

(28)

DMT = 4,4'-dimethoxytrityl 1.41 ml (11.1 mmol) of trimethylchlorosilane are added dropwise at 0° C. to a suspension of 616 mg (2.22 mmol) of compound (27) in 20 ml of absolute pyridine. After 10 min at 0° C., a spatula tipful of N,N-dimethyl-4-aminopyridine is added and the mixture is warmed to RT. After 30 min at RT (in which solution occurs), the mixture is again cooled to 0° C., 1.89 ml of isobutyric anhydride are added and it is stirred at RT for 2 h. 4.4 ml of ice-water are added and, after 15 min at 0° C. and addition of 4.4 ml of concentrated aqueous ammonia, the mixture is stirred at RT for 1 h. The residue obtained after evaporation of the solvent is chromatographed on 150 g of silica gel using a gradient of ethyl acetate/methanol 9:1 to 100% MeOH, the solid thus obtained is treated at 30°–35° C. for 2.5 h with 30 ml of methanol/concentrated ammonia (2:1),the solution is evaporated and the residue is chromatographed again using ethyl acetate/methanol (2:1). In this way, 560 mg of the $N^2$-isobutyryl derivative of compound (27) are obtained, which is contaminated with isobutyramide and is employed as such in the next step.

$^1$H-NMR (250 MHz, CD$_3$OD): inter alia 7.90 [s, 1H, C(8)$\underline{H}$]; 4.14 [d, J= 6.0 Hz, 1H, C(3')$\underline{H}$]; 3.70 [m, 2H, C(5')$\underline{H}_2$]; 2.68 [m, 1H, C$\underline{H}$(CH$_3$)$_2$]; 2.18 [d, J=14.0 Hz, 1H]; 2.06 [dd (tripletoid), J=5.5 Hz, J=5.5 Hz, 1H]; 1.90 [m, 1H]; 1.51 [dd (tripletoid), J=4.5 Hz, J=4.5 Hz, 1H]; 1.28 [m, 1H]; 1.13 [d, J=6.0 Hz, CH(C$\underline{H}_3$)$_2$].

312 μl (2.25 mmol) of absolute $N(C_2H_5)_3$, 654 mg (1.93 mmol) of 4,4'-dimethoxytrityl chloride and a spatula tipful of N,N-dimethyl-4-aminopyridine are added to a solution of 560 mg of the crude product in 30 ml of absolute pyridine and the mixture is stirred at RT. After 2 h, a further 130 mg of 4,4'-dimethoxytrityl chloride and 62 μl of $N(C_2H_5)_3$ are added. After a total of 18 h, the reaction mixture is poured into 100 ml of ice-water and 100 ml of diethyl ether, the organic phase is separated off, the aqueous phase is extracted a further three times using 50 ml of diethyl ether each time, and the combined organic extracts are dried over MgSO$_4$ and evaporated in a rotary evaporator. After flash chromatography of the residue on 180 g of silica gel using ethyl acetate/isopropanol/$N(C_2H_5)_3$ (19:1:0.02) as the eluent, 746 mg (52% based on (27)) of the title compound are obtained as a pale yellowish-coloured foam.

$^1$H-NMR (250 MHz, CD$_3$OD): inter alia 7.42 [s, 1H, C(8) $\underline{H}$]; 7.38–6.95 [m, 9H]; 6.70–6.60 [m, 4H, $\underline{H}$ aromat. o to OCH$_3$]; 4.08 [d, J=4.5 Hz, 1H, C(3')$\underline{H}$]; 3.55 [s, 6H, OC$\underline{H}_3$]; 2.55 [sextet, 1H, C$\underline{H}$(CH$_3$)$_2$]; 2.28–2.12 [m, 3H]; 1.95 [m, 1H]; 1.48 [dd (tripletoid), 1H]; 1.20 [m, 1H]; 1.07 [d, J=5.5 Hz, CH(C$\underline{H}_3$)$_2$].

Example B23

Preparation of

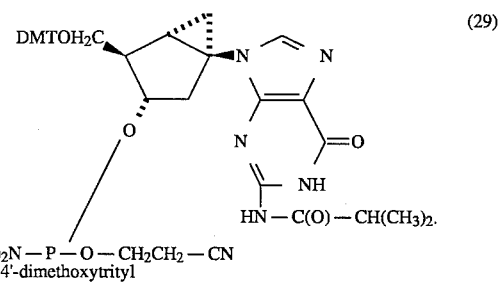

(29)

(i-propyl)$_2$N — P — O — CH$_2$CH$_2$ — CN
DMT = 4,4'-dimethoxytrityl

Analogously to Example B4, 641 mg (64%) of the title compound (diastereomer mixture) are obtained as an amorphous white powder from 740 mg (1.14 mmol) of compound (28) and 756 mg (2.51 mmol) of β-cyanoethoxy-bis(diisopropylamino)phosphine after reprecipitating three times.

$^1$H-NMR (250 MHz, CDCl$_3$): 11.97 [s, very broad, 1H, NH]; 8.87 [s, broad, ~0.5H, NH], 7.98 [s, broad, ~0.5 H, NH]; 7.55–7.25 [m, 10H]; 6.90–6.75 [m, 4H, $\underline{H}$ aromat. o to OCH$_3$]; 4.43 [m, broad, 1H, C(3')$\underline{H}$]; 3.85–3.40 [m incl. s at 3.80 (OCH$_3$), 10H]; 3.30–3.19 [m, 2H] 2.75–2.50 [m, 2H]; 2.45–2.20 [m, 3H]; 2.12–1.95 [m, 2H] 1.69, 1.52 [2×"t", 1H]; 1.40–0.95 [m, 19H].

$^{31}$P-NMR (CDCl$_3$): 148.80, 147.36.

C) Preparation of oligonucleotides

Examples C1–C4

Oligonucleotides are bound to a solid support (controlled pore glass, CPG) using the dimethoxytritylated and 3'-activated [3'-(β-cyanoethoxy-di(i-propylamino)- phosphoramidite)] nucleosides or naturally activated nucleotides of this type and the synthesis is carried out in a DNA synthesiser (Applied Biosystems, Model 380 B, standard phosphoramidite chemistry and iodine oxidation) according to the standard protocols of the manufacturer [compare also "Oligonucleotide synthesis, a practical approach" M. J. Gait; IRL Press 1984 (Oxford-Washington D.C.)]. After the coupling of the last nucleotide component, the 5'-protected oligonucleotide is detached from the support with simultaneous removal of all remaining protective groups by treatment with concentrated aqueous ammonia overnight and then purified by reverse-phase HPLC using 50 mM ammonium acetate buffer (pH 7)/acetonitrile. The 5'-dimethoxytrityl protective group is then removed by 20 minutes' treatment with 80% aqueous acetic acid, and the oligonucleotide is precipitated with ethanol and isolated by centrifugation. The purity of the oligonucleotide is checked by gel electrophoresis (polyacrylamide).

Example C1

An oligonucleotide having the sequence d(TCC AGG TGT CCG CAT C) is prepared from the compound of Example B2 (t) or B4 and the O-5'dimethoxytrityl-protected O-3'-β-cyanoethoxy-N,N-diisopropylaminophosphoramidites of the natural nucleosides 2'-deoxyadenosine (dA), 2'-deoxycytidine (dC) and 2'-deoxyguanosine (dG).

Example C2

An oligonucleotide having the sequence d(CTC GTA CCT TTC CGG TCC) is prepared from the compound of Example B2 (t) or B4 and the natural nucleosides dC, dA, dG and thymidine (dT).

Example C3

An oligonucleotide having the sequence d(TCC AGG TGT CCG TTT C) is prepared from the compound of Example B2 (t) or B4 and the natural nucleosides dA, dC, dG and dT.

Example C4

An oligonucleotide having the sequence d(CTC GTA CTT TTC CGG TCC) is prepared from the compound of Example B2 (t) or B4 and the natural nucleosides dC, dA, dG and dT.

D) Use examples

Example D1

Interaction of the oligonucleotides according to Examples C1 to C4 with complementary oligonucleotide sequences The interaction of the oligonucleotides according to Examples C1 to C4 with the corresponding base-complementary oligomers of the natural deoxy- and ribonucleotides are characterised by recording UV melting curves and the $T_m$ values determined therefrom. This standard method is described, for example, by L. A. Marky et al. in Biopolymers, 26:1601 ff (1987). A solution of the oligonucleotides according to Examples C1 to C4 and the corresponding base-complementary natural oligodeoxy- or oligoribonucleotides in 10 mM phosphate buffer, 100 mM NaCl, 0.1 mM EDTA, pH=7.0 (c=4×10$^{-6}$M/oligonucleotide) is prepared and the change in the absorption at 260 nm is recorded as a function of the temperature (15° to 95° C.). The $T_m$ value is determined from the melting curves obtained (see Table 1).

TABLE 1

| Oligomer | Oligonucleotide | $T_m$ value (°C.) | $T_m$ value (°C.)[a] |
|---|---|---|---|
| C1 | RNA | 55.1 | 62.3 |
| C1 | DNA | 53.5 | 62.5 |
| C2 | RNA | 62.4 | 63.3 |
| C2 | DNA | 58.8 | 61.7 |
| C3 | RNA | 56.3 | 59.2 |
| C3 | DNA | 53.1 | 59.0 |
| C4 | RNA | 53.4 | 56.7 |
| C4 | DNA | 49.5 | 58.1 |

[a] $T_m$ values of the unmodified (natural) analogues
RNA = complementary oligoribonucleotide
DNA = complementary oligodeoxyribonucleotide

Example D2

Interaction of the oligonucleotide according to Example C2 with base-complementary oligonucleotides.

Solutions of the oligonucleotide according to Example C2 are prepared with the corresponding base-complementary oligonucleotides of the sequences d(GGA CCG GAA YGG TAG GAG) and r(GGA CCG GAA YGG TAG GAG) in 10 mM phosphate buffer, 100 mM NaCl, 0.1 mM EDTA, pH 7, (c=4×10$^{-6}$M/oligonucleotide) and the change in the absorption at 260° C. is measured as a function of the temperature (15° C. to 95° C.). The $T_m$ value is determined from the curves. The results are indicated in Table 2.

TABLE 2

| Y | Oligonucleotide | $T_m$ value (°C.) | $T_m$ value (°C.)[a] |
|---|---|---|---|
| rA | RNA | 62.4 | 63.3 |
| dA | DNA | 58.8 | 61.7 |
| rC | RNA | 51.6 | 54.4 |
| dC | DNA | 43.1 | 46.9 |
| rG | RNA | 58.2 | 61.7 |
| dG | DNA | 53.1 | 54.8 |
| rU | RNA | 52.0 | 55.9 |
| dU | DNA | 53.5 | 55.7 |

[a] $T_m$ values of the unmodified (natural) analogues
RNA = oligoribonucleotide r(GGA CCG GAA YGG TAC GAG)
DNA = oligodeoxyribonucleotide d(GGA CCG GAA YGG TAC GAG)

Example D3

Enzymatic hydrolysis of the oligonucleotide according to Example C3.

14 μg each of the oligonucleotide according to Example C3 or of the corresponding natural oligomer are incubated at 37° C. in 200 μl of 10% heat-inactivated foetal calf serum (c=70 μg/ml). After 0.5, 1, 2, 4, 6 and 21 hours, 15 μl of the reaction solution in each case are quenched by addition to 25 μl of 9M urea and tris borate buffer (pH 7) and stored at −20° C. until measurement. The quenched reaction solutions are separated by means of polyacrylamide gel electrophoresis and the cleavage products are determined by means of the phosphorus content (phospho-imagers method). The ratio R between the sum of the concentration of the fully intact oligonucleotide ($C_n^{(t)}$) and the concentration of the fragment ($c_{n-1}^{(t)}$) formed by removal of the natural C component from the 3' end at a given time t and the starring concentration of the fully intact oligonucleotide at the time t=0 ($C_n^{(0)}$) [$R = c_n^{(t)} + c_{n-1}^{(t)}/c_n^{(0)}$] when using the oligomer according to Example C 3 is 1 (4 h), 0.98 (6 h) and 0.92 (21 h), and when using the corresponding natural oligomer having the sequence d(TTC AGG TGT CCG TTT C) is 0.11 (0.5 h), 0.05 (1 h) and 0.01 (2 h).

What is claimed is:

1. A compound of the formula I or Ia

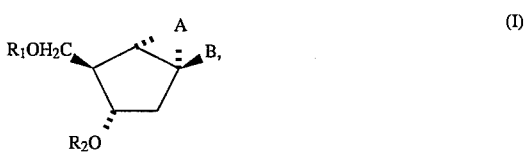

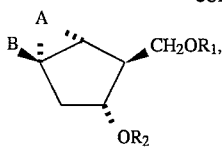

or a racemate thereof, in which A is —CH$_2$— or —CH$_2$CH$_2$—, R$_1$ is hydrogen or a protective group for alcohols, R$_2$ is hydrogen, a protective group for alcohols or a radical forming a phosphorus-containing nucleotide bridge group and B is a pyrimidine analogue, wherein the phosphorus-containing nucleotide bridge group is of the formula

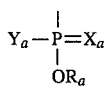

in which Y$_a$ is hydrogen, C$_1$-C$_{12}$alkyl, C$_6$-C$_{12}$aryl, C$_7$-C$_{20}$aralkyl, C$_7$-C$_{20}$alkaryl, —OR$_b$, —SR$_b$, —NH$_2$, primary amino, secondary amino, O$^\ominus$M$^\oplus$ or S$^\ominus$M$^\oplus$; X$_a$ is oxygen or sulfur; R$_a$ is hydrogen, M$^\oplus$, C$_1$-C$_{12}$alkyl, C$_2$-C$_{12}$alkenyl or C$_6$-C$_{12}$aryl, the group R$_a$O— is N-heteroaryl-N-yl having 5 ring members and 1 to 3N atoms; R$_b$ is hydrogen, C$_1$-C$_{12}$alkyl or C$_6$-C$_{12}$aryl; and M$^\oplus$ is Na$^\oplus$, K$^\oplus$Li$^\oplus$, NH$_4^\oplus$ or primary, secondary, tertiary or quaternary ammonium; where alkyl, aryl, aralkyl and alkaryl in Y$_a$, R$_a$ and R$_b$ are unsubstituted or substituted by alkoxy, alkylthio, halogen, —CN, —NO$_2$, phenyl, nitrophenyl or halophenyl, and the pyrimidine analogue B is a uracil, thymine or cytosine radical of the formulae III, IIIa or IIIb

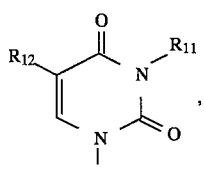

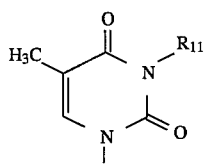

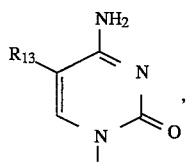

in which R$_{11}$ is H or C$_1$-C$_4$alkyl, and R$_{12}$ R$_{13}$ independently of one another are H, OH, SH, NH$_2$, NHNH$_2$, NHOH, NHOalkyl having 1 to 12 C atoms, F, Cl, Br, alkyl or hydroxyalkyl or aminoalkyl or alkoxy or alkylthio having 1 to 12 C atoms, where the hydroxyl and amino groups are unsubstituted or substituted by a protective group, phenyl, benzyl, primary amino having 1 to 20 C atoms or secondary amino having 2 to 30 C atoms, and the hydrogen atoms of the NH$_2$ group in formula IIIb are unsubstituted or substituted by C$_1$-C$_6$alkyl, benzoyl or benzyl, or a dihydro derivative of a radical of the formula III, IIIa or IIIb.

2. A compound according to claim 1, wherein R$_1$ and R$_2$ are each hydrogen.

3. A compound according to claim 1, wherein A is —CH$_2$—.

4. A compound according to claim 1, wherein R$_1$ and R$_2$ are independently of one another linear or branched C$_1$-C$_8$alkyl, C$_7$-C$_{18}$aralkyl, triphenylsilyl, alkyldiphenylsilyl, dialkylphenylsilyl or trialkylsilyl having 1 to 20 C atoms in the alkyl groups, —(C$_1$-C$_8$alkyl)$_2$Si—O—Si(C$_1$-C$_8$alkyl)$_2$—, C$_2$-C$_{12}$acyl, R$_3$—SO$_2$—, in which R$_3$ is C$_1$-C$_{12}$alkyl, C$_5$— or C$_6$cycloalkyl, phenyl, benzyl, C$_1$-C$_{12}$alkylphenyl, C$_1$-C$_{12}$alkylbenzyl, or are C$_1$-C$_{12}$alkoxycarbonyl, phenoxycarbonyl, benzyloxycarbonyl, methylphenoxycarbonyl or methylbenzyloxycarbonyl which is unsubstituted or substituted by F, Cl, Br, C$_1$-C$_4$alkoxy, tri(C$_1$-C$_4$alkyl)silyl or C$_1$-C$_4$alkylsulfonyl, or 9-fluorenylmethoxycarbonyl.

5. A compound according to claim 4, wherein R$_1$ and R$_2$ independently of one another are linear or branched C$_1$-C$_4$alkyl, C$_7$-C$_{18}$aralkyl, trialkylsilyl having 1 to 12 C atoms in the alkyl groups, —(CH$_3$)$_2$Si—O—Si(CH$_3$)$_2$—, —(i—C$_3$H$_7$)$_2$Si—O—Si(iC$_3$H$_7$)$_2$—, C$_2$-C$_8$acyl, R$_3$—SO$_2$—, in which R$_3$ is C$_1$-C$_6$alkyl, phenyl, benzyl, C$_1$-C$_4$alkylphenyl, C$_1$-C$_4$alkylbenzyl, halophenyl or halobenzyl, or are C$_1$-C$_8$alkoxycarbonyl, phenoxycarbonyl, benzyloxycarbonyl or 9-fluorenylmethoxycarbonyl.

6. A compound according to claim 4, wherein R$_1$ and R$_2$ independently of one another are methyl, ethyl, n- or i-propyl, n-, i- or t-butyl; benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(methoxyphenyl)(phenyl)methyl, trityl, tri(methylphenyl)methyl, tri(dimethylphenyl)methyl, tri(methoxyphenyl)methyl, tri(dimethoxyphenyl)methyl; trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl, —(CH$_3$)$_2$Si—O—Si(CH$_3$)$_2$—, —(i—C$_3$H$_7$)$_2$Si—O—Si(iC$_3$H$_7$)$_2$—; acetyl, propanoyl, butanoyl, pentanoyl, hexanoyl, benzoyl, methylbenzoyl, methoxybenzoyl, chlorobenzoyl or bromobenzoyl; methyl-, ethyl-, propyl-, butyl-, phenyl-, benzyl-, p-bromo-, p-methoxy- or p-methylphenylsulfonyl; methoxy-, ethoxy-, n- or i-propoxy- or n-, i- or t-butoxycarbonyl, or phenoxycarbonyl, benzyloxycarbonyl, methyl- or methoxy- or chlorophenoxycarbonyl or -benzyloxycarbonyl or 9-fluorenylmethoxycarbonyl.

7. A compound according to claim 1, wherein R$_1$ and R$_2$ are the same protective groups.

8. A compound according to claim 1, in which R$_{12}$ is H, C$_1$-C$_6$alkyl or -hydroxyalkyl, F, Cl, Br, NH$_2$, benzoylamino, mono- or di-C$_1$-C$_6$-alkylamino.

9. A compound according to claim 1, in which R$_{13}$ is H, C$_1$-C$_6$alkyl or -alkoxy or -hydroxyalkyl, F, Cl, Br, NH$_2$, benzoylamino, mono- or di-C$_1$-C$_6$-alkylamino.

10. A compound according to claim 8, in which R$_{12}$ is H, F, Cl, Br, NH$_2$, NHCH$_3$, N(CH$_3$)$_2$ or C$_1$-C$_4$alkyl.

11. A compound according to claim 9, in which R$_{13}$ is H, C$_1$-C$_4$alkyl, NH$_2$, NHCH$_3$ or (CH$_3$)$_2$N.

12. A compound according to claim 1, in which B as the radical of a pyrimidine analogue is derived from uracil, thymine, cytosine, 5-fluorouracil, 5-chlorouracil, 5-bromouracil, dihydrouracil or 5-methylcytosine.

13. A compound according to claim 1, wherein X$_a$ is O, R$_a$ is β-cyanoethyl, and Y$_a$ is di(i-propyl)amino.

* * * * *